United States Patent [19]

Rojko et al.

[11] Patent Number: 5,591,717

[45] Date of Patent: Jan. 7, 1997

[54] BRANCHED APOGENIC PEPTIDE FOR INDUCING APOPTOSIS

[76] Inventors: Jennifer L. Rojko, 5 Duke Ct., Rockville, Md. 20850; James R. Hartke, 3865 Alton Darby Rd., Hilliard, Ohio 43026; Carolyn M. Cheney, 351 ½ W. Hubbard Ave., Columbus, Ohio 43215

[21] Appl. No.: 224,632

[22] Filed: Apr. 6, 1994

[51] Int. Cl.[6] ............................ A61K 38/00; C07K 5/00; C07K 7/00; C07K 17/00

[52] U.S. Cl. ..................... 514/12; 514/13; 514/14; 514/15; 514/16; 514/17; 530/324; 530/325; 530/326; 530/327; 530/328; 530/329; 435/29

[58] Field of Search ..................... 435/29; 514/12–13, 514/14–17; 530/324, 325, 326, 330, 327, 328, 329

[56] References Cited

U.S. PATENT DOCUMENTS

| | | | |
|---|---|---|---|
| 5,017,691 | 5/1991 | Lee et al. | 530/351 |
| 5,144,006 | 9/1992 | Tam | 530/345 |
| 5,229,490 | 7/1993 | Tam | 530/324 |

FOREIGN PATENT DOCUMENTS 11778  10/1990  WIPO.

OTHER PUBLICATIONS

On–Line Search, 5 pages listing 6 patents and/or patent applications with abstract.

"Multiple Antigen Peptide," Tam et al., *Journal of Immunological Methods*, 124, pp. 53–61, Nov. 13, 1989.

"Chemically Unambiguous Peptide Immunogen: Preparation, Orientation and Antigenicity of Purified Peptide Conjugated to the Multiple Antigen Peptide System," *Molecular Immunology*, vol. 28, No. 6, pp. 623–630, Jun. 1991.

Dhein J. Daniel P T. Trauth B C, Oehm A. Moller P., Krammer P H., "Induction of Apoptosis by Monoclonal Antibody Anti–Apo–1 Class Switch Variants is Dependent on Cross–Linking of Apo–1 Cell Surface Antigens," *J. Immunol*, 149:3166–3173, 1992.

Donahue P R, Quackenbush S L, Gallo M V, DeNoronha C M C, Overbaugh J. Hoover E A, Mullins J I, "Viral Genetic Determinants of T–Cell Killing and Immunodeficiency Disease Induction by the Feline Leukemia Virus FeLV–FAIDS", *J. Virol*, 65(8):4461–4469, 1991.

Duvall E, Wyllie A H, "Death and the Cell," *Immunology Today*, 7(4):115–19, 1986.

Edelman G M, "Morphoregulatory Molecules," *Biochemistry*, 27(10):3533–3543, 1988.

Hinrichsen R D, Blackshear P J, "Regulation of Peptide–Calmodulin Complexes by Protein Kinase C in Vivo," *Proc. Natl. Acad. Sci. USA*, 90:1585–1589, 1993.

Hooper, C., "Apoptosis: The Birth of Cell Death," *J. NIH Res.*, 2:46–48, 1990.

Iwata M, Mukai M, Nakai Y, Iseki R, "Retinoic Acids Inhibit Activation–Induced Apoptosis in T Cell Hybridomas and Thymocytes," *J. Immunol.*, 149(10):3302–3308, 1992.

Koury M J, Bondurant M C, "Erythropoietin Retards DNS Breackdown and Prevents Programmed Death in Erythroid Progenitor Cells," *Science*, 248:378–381, 1990.

Li J–P, Andrea A D, Lodish H F, Baltimore D, "Activation of Cell Growth by Binding of Friend Spleen Focus–Forming Virus gp55 Glycoprotein to the Erythropoietin Receptor," *Nature*, 343:761–764, 1990.

Marin, S J, Lennon S V, Bonham A M, and Cott T G, "Induction of Apoptosis (Programmed Cell Death) in Human Leukemia HL–60 Cells by Inhibition of RNA or Protein Synthesis," *J. Immunol.*, 145:1859–1867, 1990.

Marguerite M, Bossus M, Mazingue C, Wolowczuk I, Gras–Masse H, Tartar A, Capron A, Auriault C, "Analysis of Antigenicity and Immunogenicity of Five Different Chemically Defined Constructs of a Peptide," *Mol. Immunol.*, 29(6):793–800, 1992.

McConkey D J, Hartzell P, Amador–Perez J F, Orrenius S, Jondal M, "Calcium–Dependent Killing of Immature Thymocytes by Stimulation Via the CD3/T Cell Receptor Complex," *J. Immunol.*, 143(6):1801–1806, 1989.

McConkey D J, Hartzel P, Nicotera P, Orrenius S, "Calcium–Activated DNA Fragmentation Kills Immature Thymocytes," *FASEB J.*, 3:1843:1849, 1989.

McConkey D J, Hartzell P. Duddy S K, Hakansson H, Orreinus S, "2,3,4,8–Tetrachlorodibenzo–p–dioxin Kills Immature Thmocytes by Ca2+–mediated Endonuclease Activation," *Science*, 242:256–259, 1988.

Meyaard L, Otto S A, Jonkey R R, Mijnster M J, Keet R P M, Miedema F, "Programmed Cell Death of T Cells in HIV–1 Infection," *Science*, 257:217–219, 1992.

Miller, M A, Montelaro R C, "Amphipathic Helical Segments of Human Immunodeficiency Virus Type I Transmembrane Proteins and Their Potential Role in Viral Cytopathicity In: Membrane Interactions of HIV", Wiley–Liss, Inc., pp. 351–364, 1992.

Miller M A, Gary R F, Jaynes J M, Montelaro R C, "A Structural Correlation Between Lentivirus Transmembrane Proteins and Natural Cytolytic Peptides," *AIDS Res. Human Retrov.*, 7(6):511–519, 1991.

Nieto M A, Lopez–Rivas A, "Il–2 Protects T Lymphocytes From Glucocorticoid–Induced DNA Fragmentation and Cell Death," *J. Immunol.*, 143(12):4166–4170, 1989.

(List continued on next page.)

*Primary Examiner*—Toni R. Scheiner
*Assistant Examiner*—Sheela J. Huff

[57] ABSTRACT

The present invention provides a new branched apogenic peptide for inducing apoptosis in non-quiescent cells. The branched apogenic peptide comprises an amino acid core of at least three and preferably seven amino acids. Preferable the core amino acids are lysine molecules. Attached to the core are at least four, preferably eight identical peptide chains comprising the following amino acids in the following order:

z x x z wherein: Z is arginine, lysine, or any synthetic positively charged amino acid; and X is any amino acid. The invention also relates to a method of inducing apoptosis.

18 Claims, 17 Drawing Sheets

OTHER PUBLICATIONS

Noteborn M H M, Todd D. Verschueren C A J, deGauw H W F M, Curran W L, Veldkamp S, Douglas A J, McNulty M S, van der Eb A J, Koch G, "A Single Chicken Anemia Virs Protein Induces Apoptosis," *J. Virol.*, 68(1):346–351, 1994.

Payne Me, Fong Y–L, Ono T, Colbran R J, Kemp B E, Soderling T R, Means A R, "Calcium/Calmodulin–Dependent Protein Kinase II," *J. Biol. Chem.*, 263(15)7190–7195, 1988.

Riedel N, Hoover E A, Dornsife R E, Mullins J I, "Pathogenic and Host Range Determinants of Feline Aplastic Anemia Retrovirus," *Proc. Natl. Acad. Sci. USA*, 85:2758–2762, 1988.

Rigby Ma, Rojko J L, Stewart Ma, Kociba G J, Cheney C M, Rezanka L J, Mathes L E, Hartke J R, Jarrett O, Neil J C, "Parial Dissociation of Subgroup C Phenotype and In Vivo Behavior in Feline Leukaemia Viruses With Chimeric Envelope Genes," *J. Gen. Virol.*, 73:2839–2847, 1992.

Rojko J L, Fulton R M, Rezanka L J, Williams L L, Copelan E, Cheney C M, Reichel G S, Neil J C, MAthes L E, Fisher T G, Cloyd M W, "Lymphocytotoxic Strains of Feline Leukemia Virus Induce Apoptosis in Feline T4–Thymic Lymphoma Cells," *Lab Invest.*, 66(4):418, 1992.

Rojko J L, Kociba G J, Abkowitz J L, Hamilton K L, Hardy W D Jr, Ihle J N, O'Brien S J, "Feline Lymphomas: Immunological and Cytochemical Characterization," *Cancer Res.*, 49:345–51, 1989.

Sachs L, Lotem J, "Control of Programmed Cell Death in Normal and Leukemia Cells: New Implications for Therapy," *Blood*, 82(1):15–21, 1993.

Smith C A, Williams G T, Kingston R, Jenkinson E J, Owen J J T, "Antibodies to CD3/T–Cell Receptro Complex Induce Death by Apoptosis in Immature T Cells in Thymic Cultures," *Nature*, 337:181–184, 1989.

Spencer D M, Wandless T J, Schreiber S L, Crabtree G R, "Controlling Signal Transduction With Synthetic Ligands," *Science*, 262:1019–1024, 1993.

Vaux D L, "Toward an Understanding of the Molecular Mechanisms of Physiological Cell Death," *Proc. Natl. Acad. Sci. USA*, 90:786–789, 1993.

Kumar et al. J. Virology vol. 63 p. 2379 (1989).

Nicolaisen–Strouss et al J. Virology vol. 61 p. 3410 (1987).

Overbaugh et al Science vol. 239, p. 906 (1988).

Varquez et al, Eur. J. Immunol. vol. 21 p. 231 (1991).

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 15 base pairs
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:1:

```
Leu Cys Asn Lys Thr Gln Lys Gly His Lys Gly Thr His Tyr Leu
1               5                   10                  15
```

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:2:

```
Glx Xaa Xaa Glx
1
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:3:

```
Leu Cys Lys Lys Thr Gln Lys Gly His Lys Gly Thr His Tyr Leu
1               5                   10                  15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO (xi) SEQUENCE DESCRIPTION: SEQ ID NO:4:

Leu Cys Asn Lys Thr Gln Lys Gly His Arg Gly Thr His Tyr Leu
1               5                   10                  15

(2) INFORMATION FOR SEQ ID NO:5:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (iii) HYPOTHETICAL: NO (xi) SEQUENCE DESCRIPTION: SEQ ID NO:5:

Leu Cys Lys Lys Thr Gln Lys Gly His Arg Gly Thr His Tyr Leu
1               5                   10                  15

(2) INFORMATION FOR SEQ ID NO:6:

(i) SEQUENCE CHARACTERISTICS:
    (A) LENGTH: 7 amino acids
    (B) TYPE: amino acid
    (D) TOPOLOGY: linear (ii) MOLECULE TYPE: peptide (iii) HYPOTHETICAL: NO (ix) SEQUENCE DESCRIPTION: SEQ ID NO:6:

Glx Xaa Xaa Glx Xaa Xaa Glx
1               5

BRANCHED APOGENIC PEPTIDE FOR INDUCING APOPTOSIS

BACKGROUND OF THE INVENTION

Under normal conditions in adult organisms, cellular number is tightly controlled; cell multiplication equals cell death. The process where cells differentiate and die, known as apoptosis is poorly understood. Apoptosis is significant biological event, particularly in situations where apoptosis fails to occur or occurs at inappropriate times. For example, in cancers, apoptosis fails to occur and the cancer cells fail to die. The cells continue to accumulate, eventually leading to the death of the host organism.

There are also situations where the onset of apoptosis is accelerated. Infection by certain viruses, such as HIV or feline leukemia virus, induces immune suppression by the activation of existing apoptotic pathways.

It is desirable to have the ability to induce apoptosis in cells particularly to study the process and the effects of apoptosis. Certain agents, that is, apogens, are known to induce apoptosis, but typically in a limited manner. Some conventional apogens such as radiation, damage cells by inducing direct DNA damage. Other apogens, such as actinomycin D, inhibit protein synthesis at the level of transcription, whereas cycloheximide inhibits protein synthesis at the level of translation. However these conventional apogens greatly disrupt cellular function and not act through natural pre-existing pathways.

It would be particularly desirable to have an agent that induces apoptosis, particularly in cancerous cells, mitogen-stimulated proliferating cells, and other non-quiescent cells.

SUMMARY OF THE INVENTION

The present invention provides a new branched apogenic peptide for inducing apoptosis in non-quiescent cells. The branched apogenic peptide comprises an amino acid core of at least three and preferably seven amino acids. Preferable the core amino acids are lysine molecules. Attached to the core are at least four, preferably eight identical peptide chains comprising the following amino acids in the following order:

Z X X Z wherein: Z is arginine, lysine, or any synthetic positively charged amino acid; and X is any amino acid. The invention also relates to a method of inducing apoptosis.

BRIEF DESCRIPTION OF THE DRAWINGS

FIG. 1A is a graph showing the effect of $C_{Sarma}$VR5-BAP on 3201 control cells uninfected by FeLV virus; the square represents AVR5-BAP 2.7 μM; the diamond represents CVR5-BAP 2.7 μM; the triangle represents CVR5-BAP 1.3 μM; the square represents CVR5-BAP 0.7 μM; the upside down triangle represents CVR5-BAP 0.35 μM; the colored circle represents CVR5-BAP 0.17 μM; and the uncolored circle represents no peptide.

FIG. 1B is a graph showing the effect of $C_{Sarma}$VR5-BAP on 3201-FeLV-A $_{Glasgow1}$-infected cells; the square represents AVR5-BAP 2.7 μM; the diamond represents CVR5-BAP 2.7 μM; the triangle represents CVR5-BAP 1.3 μM; the square represents CVR5-BAP 0.7 μM; the upside down triangle represents CVR5-BAP 0.35 μM; the colored circle represents CVR5-BAP 0.17 μM; and the uncolored circle represents no peptide.

FIG. 1C is a graph showing the effect of $C_{Sarma}$VR5-BAP on 3201 FeLV-$C_{Sarma}$ infected cells; the square represents AVR5-BAP 2.7 μM; the diamond represents CVR5-BAP 2.7 μM; the triangle represents CVR5-BAP 1.3 μM; the square represents CVR5-BAP 0.7 μM; the upside down triangle represents CVR5-BAP 0.35 μM; the colored circle represents CVR5-BAP 0.17 μM; and the uncolored circle represents no peptide.

FIG. 2 is a graph showing the effect of $C_{Sarma}$VR5-BAP on HL60 cells; the upside down colored triangle represents 0.5 μM; the colored square represents 1.0 μM CVR5-BAP; the colored triangle represents 1.9 μM CVR5-BAP; the colored diamond represents 3.8 μM CVR5-BAP; the small uncolored circle represents 7.5 μM CVR5-BAP; the big uncolored circle represents 15 μM CVR5-BAP; the big colored circle represents 30 μM CVR5-BAP; the uncolored square represents no peptide; the uncolored diamond represents 15 μM AVR1-BAP; the uncolored triangle represents 15 μM I26-BAP; and the uncolored upside down triangle represents 15 μM AVR5-BAP.

FIG. 3 is a graph showing the effect of $C_{Sarma}$VR5-BAP on H9 cells; the upside down colored triangle represents 0.5 μM; the colored square represents 1.0 μM CVR5-BAP; the colored triangle represents 1.9 μM CVR5-BAP; the colored diamond represents 3.8 μM CVR5-BAP; the small uncolored circle represents 7.5 μM CVR5-BAP; the big uncolored circle represents 15 μM CVR5-BAP; the big colored circle represents 30 μM CVR5-BAP; the uncolored square represents no peptide; the uncolored diamond represents 15 μM AVR1-BAP; the uncolored triangle represents 15 μM I26-BAP; and the uncolored upside down triangle represents 15 μM AVR5-BAP.

FIG. 4 is a graph showing the effect of $C_{Sarma}$VR5-BAP on K562 cells; the upside down colored triangle represents 0.5 μM; the colored square represents 1.0 μM CVR5-BAP; the colored triangle represents 1.9 μM CVR5-BAP; the colored diamond represents 3.8 μM CVR5-BAP; the small uncolored circle represents 7.5 μM CVR5-BAP; the big uncolored circle represents 15 μM CVR5-BAP; the big colored circle represents 30 μM CVR5-BAP; the uncolored square represents no peptide; the uncolored diamond represents 15 μM AVR1-BAP; the uncolored triangle represents 15 μM I26-BAP; and the uncolored upside down triangle represents 15 μM AVR5-BAP.

FIG. 5 is a graph showing the effect of $C_{Sarma}$VR5-BAP on F422 cells; the uncolored square represents AVR5-BAP 2.7 μM; the diamond represents CVR5-BAP 2.7 μM; the triangle represents CVR5-BAP 1.3 μM; the colored square represents CVR5-BAP 0.7 μM; the upside down triangle represents CVR5-BAP 0.35 μM; the colored circle represents CVR5-BAP 0.17 μM; and the uncolored circle represents no peptide.

FIG. 6 is a graph showing the effect of $C_{Sarma}$VR5-BAP on MCC cells; the uncolored square represents AVR5-BAP 2.7 μM; the diamond represents CVR5-BAP 2.7 μM; the triangle represents CVR5-BAP 1.3 μM; the colored square represents CVR5-BAP 0.7 μM; the upside down triangle represents CVR5-BAP 0.35 μM; the colored circle represents CVR5-BAP 0.17 μM; and the uncolored circle represents no peptide.

FIG. 7 is a graph showing the effect of $C_{Sarma}$VR5-BAP on U937 cells; the uncolored square represents AVR5-BAP 2.7 μM; the diamond represents CVR5-BAP 2.7 μM; the triangle represents CVR5-BAP 1.3 μM; the colored square represents CVR5-BAP 0.7 μM; the upside down triangle represents CVR5-BAP 0.35 μM; the colored circle represents CVR5-BAP 0.17 μM; and the uncolored circle represents no peptide.

FIG. 11 is a graph showing the effect of $C_{Sarma}$VR5-BAP on human keratinocytes; the square represents AVR5-BAP 3.5 μM; the diamond represents CVR5-BAP 3.5 μM; the triangle represents CVR5-BAP 1.7 μM; the square represents CVR5-BAP 0.7 μM; the upside down triangle represents CVR5-BAP 3.5 μM; the colored circle represents CVR5-BAP 1.7 μM; and the uncolored circle represents no peptide.

Figure 14:
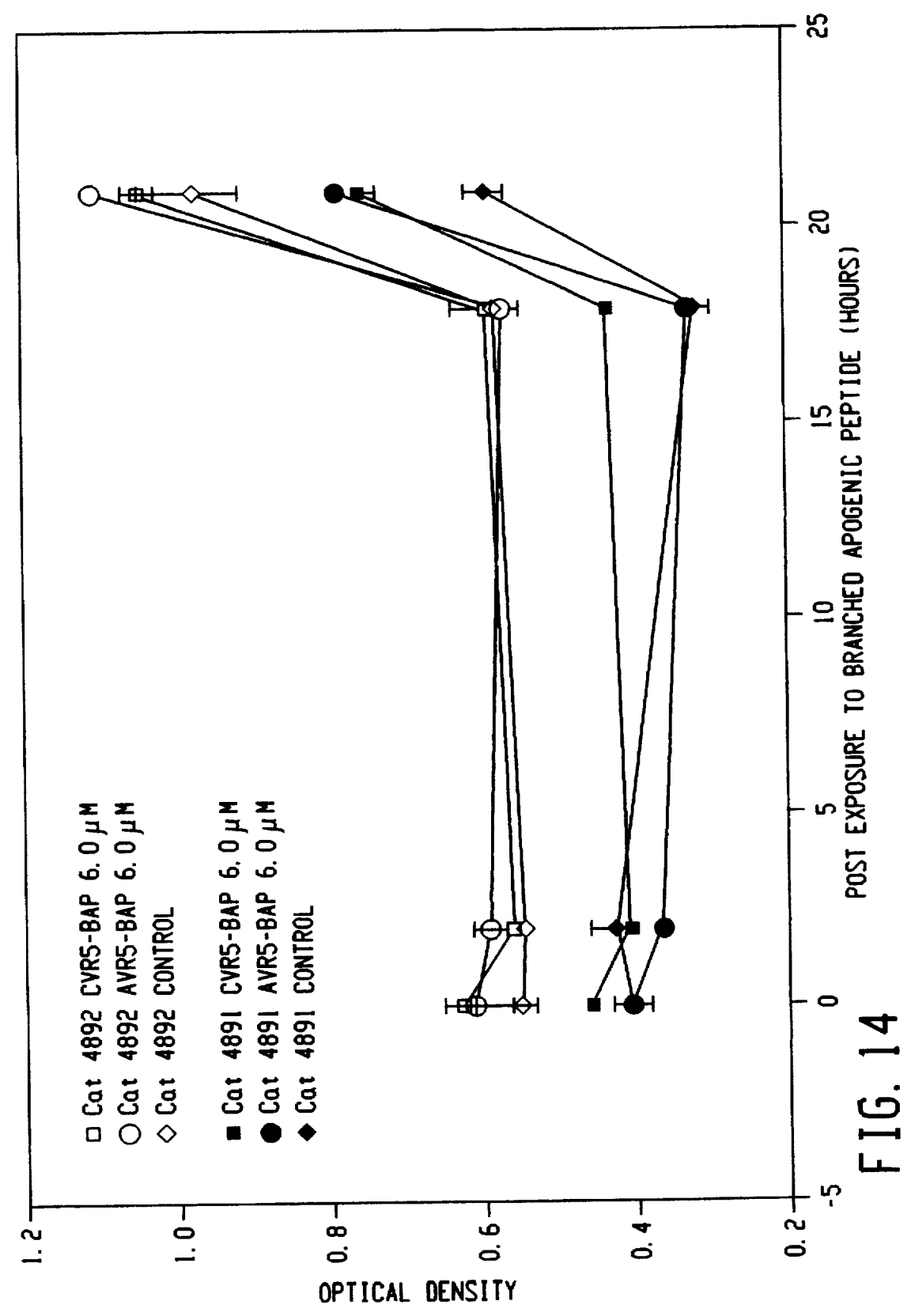
Figure 15:
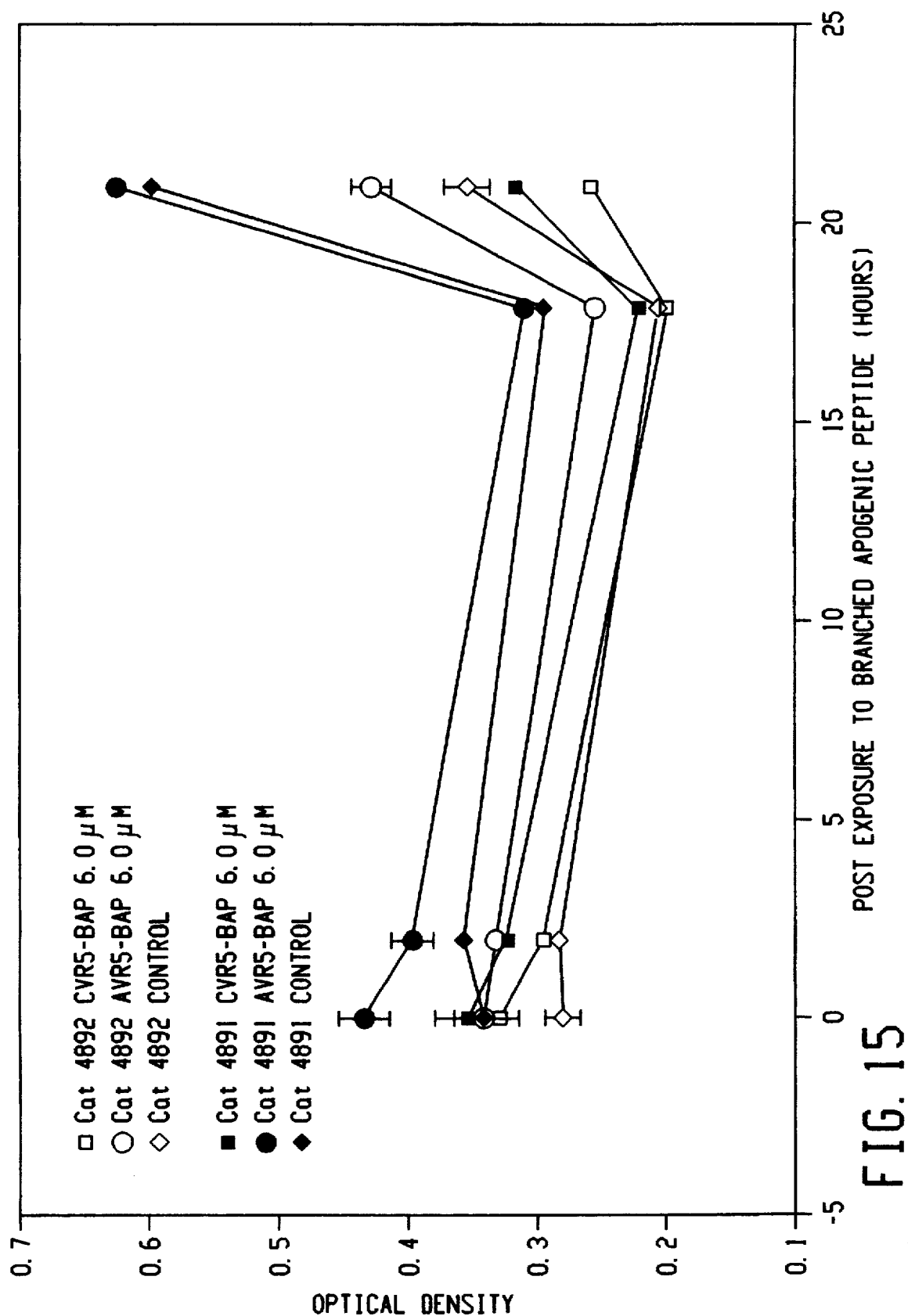

FIG. 14 is a graph showing the effect of $C_{Sarma}$VR5-BAP on feline primary bone marrow cells; the uncolored square represents cat 4892 CVR5-BAP 5.0 μM; the uncolored circle represents cat 4892 AVR5-BAP 6.0 μM; the uncolored diamond represents cat 4892 control; the colored square represents cat 4891 CVR5-BAP 6.0 μM; the colored circle represents cat 4891 AVR5-BAP 6.0 μM; and the colored diamond represents cat 4891 control; and FIG. 15 is a graph showing the effect of $C_{Sarma}$VR5-BAP on feline primary thymocytes; the uncolored square represents cat 4892 CVR5-BAP 5.0 μM; the uncolored circle represents cat 4892 AVR5-BAP 6.0 μM; the uncolored diamond represents cat 4892 control; the colored square represents cat 4891 CVR5-BAP 6.0 μM; the colored circle represents cat 4891 AVR5-BAP 6.0 μM; and the colored diamond represents cat 4891 control.

DETAILED DESCRIPTION OF THE INVENTION

The present invention provides a new branched apogenic peptide which is particularly useful for inducing apoptosis in non-quiescent cells, and may be employed in a variety of scenarios including research.

An amino acid sequence, designated "$C_{Sarma}$VR5" has been discovered in the $C_{Sarma}$ feline leukemia virus envelope glyco-protein (gp70), variable region 5, that confers upon the FeLV $C_{Sarma}$ clone the ability to induce apoptosis in leukemia cells and other nonquiescent cells. However, it has also been discovered that in its isolated form, the peptide corresponding to the sequence does not induce apoptosis in cells. In order to provide an apoptosis inducing agent, the $C_{Sarma}$VR5 sequence has been incorporated into a branched apogenic peptide. The branched apogenic peptide, (also referred to herein as a "BAP") contains a core of amino acids, preferably at least one amino acid, more preferably three amino acids, most preferably seven amino acids. While any amino acid may be used for the core, lysine molecules are preferred. Attached to the core are peptides, preferably eight identical peptides. The branched apogenic peptides are 1 kd to 50 kd, preferably, 12 kd to 15 kd in size. The branched apogenic peptides may cross link cell surface receptors. The structure of the preferred branched apogenic peptide is shown below:

```
                        VR5 peptide
                   LYS
                  /    \VR5 peptide
               LYS
              /    \    /VR5 peptide
                   LYS
             /         \VR5 peptide
          LYS
             \         /VR5 peptide
                   LYS
              \    /    \VR5 peptide
               LYS
                  \    /VR5 peptide
                   LYS
                        \VR5 peptide
```

Several branched apogenic peptides which induce apoptosis have been discovered and synthesized. One branched apogenic peptide, designated "$C_{Sarma}$VR5-BAP" contains eight $C_{Sarma}$VR5 peptides attached to the lysine core. Another branched apogenic peptide, designated "CVR5N3-BAP" contains eight CVR5N3 peptides attached to the lysine core. The branched apogenic peptide designated "ENCFE6VR5-BAP" contains eight ENCFE6VR5 peptides attached to the lysine core. The branched apogenic peptide designated "ENCFE6VR5K3-BAP" contains eight ENCFE6VR5K3 peptides attached to the lysine core.

The peptides are preferably 4 to 40, more preferably 7 to 25 amino acids in length, most preferably 10 to 15 amino acids in length. The peptide comprises the following four amino acids in the sequence shown below:

Z X X Z SEQ.ID.NO:2 wherein: Z is arginine, lysine or any positively charged synthetic amino acid; and X is any amino acid.

Preferably, the peptide comprises the following seven amino acids in the sequence shown below:
Z X X Z X X Z (SEQ.ID.NO:6
wherein: Z is arginine or lysine; and X is any amino acid.

Several peptides have been synthesized which contain the preferred amino acids. The peptide designated "$C_{Sarma}$-VR5" has the following sequence and is the preferred peptide:
L C K K T Q K G H K G T H Y L SEQ.ID.NO:3
wherein: K is lysine, T is threonine, L is leucine, C is cysteine, Q is glutamine, G is glycine, H is histidine, and Y is tyrosine. The $C_{Sarma}$-VR5 peptide alone does not induce apoptosis.

The peptide designated "CVR5N3" has the following amino acid sequence:

"L C N K T Q K G H K G T H Y L SEQ.ID.NO.1"

wherein: K is lysine, T is threonine, L is leucine, C is cysteine, Q is glutamine, G is glycine, H is histidine, N is asparagine; and Y is tyrosine.

The peptide designated "ENCFE6VR5" has the following amino acid sequence:

L C N K T Q K G H R G T H Y L  SEQ.ID.NO.4 wherein: K is lysine, T is threonine, L is leucine, C is cysteine, Q is glutamine, G is glycine, H is histidine, N is asparagine, R is arginine, and Y is tyrosine.

The peptide designated "ENCFE6VR5K3" has the following amino acid sequence:

L C K K T Q K G H R G T H Y L  (SEQ.ID.NO.5 wherein: K is lysine, T is threonine, L is leucine, C is cysteine, Q is glutamine, G is glycine, H is histidine, R is arginine, and Y is tyrosine.

Materials and Methods

Comparative Branched Apogenic Peptides

In addition to the branched apogenic peptide which induce apoptosis, two branched non-apogenic peptides, were frequently added to cell cultures for comparison, "$A_{Glasgow1}$VR5-BNP", "I26-CB," and "1161CVR5-BNP". $A_{Glasgow1}$VR5-BNP has the seven lysine core to which eight $A_{Glasgow1}$VR5 peptides have been attached. The $A_{Glasgow1}$VR5 is a peptide that corresponds to variable region five from feline leukemia virus $A_{Glasgow1}$, the pFGA.5 clone. $A_{Glasgow1}$VR5 has the following sequence:

L C N K T Q Q G H T G A H Y L

The 1161CVR5-BNP has the seven lysine core to which eight 1161CVR5 peptides have been attached. The peptide 1161CVR5-BNP corresponds to the variable region five sequence of the feline leukemia virus 1161C isolate and has the following sequence:

L C N K T H Q G H T G A D Y L T A P R Y L A A P N

Synthesis of Peptide Chains

The peptide chains which were free and not attached to either a branched apogenic peptide or a branched non-apogenic peptide, were synthesized according to conventional methods on an Applied Biosystems 430A automated synthesizer, operating on an initial scale of 0.20 to 0.25 mol, following the manufacturer's instructions. The peptide chains were synthesized using the t-butoxycarbonyl/benzyl (BOC)/Bzl) strategy on a solid phase support. The product was released from the support by reaction with anhydrous hydrogen fluoride, passed over a Sephadex G-50 column for an initial purification, and lyophilized. Purity of peptide chain preparation was estimated to be 90% or greater. Initial yield was in the range of 200 to 300 mg before purification. Peptide chains were characterized by amino acid composition determination after acid hydrolysis and phenylisothiocyanate derivitization followed by reverse phase high performance liquid chromatography (Pico-tag system, Waters Chromatography).

These free peptides are useful in the study of apoptosis, particularly as comparative agents.

Synthesis of Branched Apogenic Peptides and the Branched Non-Apogenic Peptides

The branched apogenic peptides and the branched non-apogenic peptides were constructed according to the method in Tam et al., "Multiple Antigen Peptide," *J. Immun. Meth.*, 124:53, (1989); and Yi-Ann et al., "Chemically Unambiguous Peptide Immunogens," *Mol. Immun.*, 28:623, (1991); using an Applied Biosystems 430A automated synthesizer operating on an initial scale of 0.20 to 0.25 mol, according to the manufacturer's instructions. First, the lysine core was synthesized by attaching a single lysine molecule to the solid phase support peptidylphenylacetamidomethyl-polystyrene resin and deprotecting both the α and Epsilon amino groups of the first lysine molecule. The second tier was constructed when a second and third lysine molecule were attached via their carboxyl groups to each amino group of the first lysine residue. The α and Epsilon amino groups of the second and third lysine molecules were deprotected to provide a total of four amino groups. The third tier was constructed when four more lysine molecules were attached to the four amino groups to produce a core of seven lysine molecules. The α and Epsilon amino groups of the third tier were deprotected to provide eight free amino groups. Eight peptide chains were attached via the terminal carboxyl group to the eight free amino groups.

More specifically, the branched apogenic peptides were directly synthesized upon a three tier lysine core, branching from an H-Cys, that is an acetamidomethyl, $CH_3CONHCH_2$)-B-Ala-MBHA-polystyrene resin, essentially according to Tam. The residue of B-Ala was included as a diagnostic for amino-acid composition analysis. The masked residue of Cys remained in the branched apogenic peptides.

The fully protected sequences were made using the Applied Biosystems 430A automated synthesizer, operating on an initial scale of 0.2–0.25 mol, providing for the initial branched apogenic peptide in the range 200–300 mg. The BOC/Bzl method of peptide synthesis were employed. The reaction conditions mitigated against chain aggregation and the sequelae deleterious to the efficiency of sequence development. Chain growth was monitored by selected analyses of intermediate resin-bound peptide for residual amine following acylation, and for amino acid composition.

The peptides were synthesized utilizing the t-butoxycarbonyl/benzyl (BOC/Bzl) protecting group method of the Merrifield 'solid-phase' stepwise strategy for peptide synthesis, with the exceptions of the use of the trifluoracetyl and acetamidomethyl protecting groups. That is, the temporary N-alpha protecting group for all amino-acids was BOC, with side-chain protection as follows: arginine, tosyl; systeine, 4-methylbenzyl; serine and threonine, benxyl; aspartic and glutamic acids, benzyl ester; histidine, 2,4-dinitrophenol; lysine, 4-chlorobenzyloxycarbonyl; methionine, sulfoxide; tyrosine, 2-bromobenzyloxycarbonyl; tryptophan, formyl. The Applied Biosystems Model 430A automated peptide synthesizer was employed using protected peptidylphenylacetamidomethylpolystyrene resin. The manufacturer's instructions were followed for long chain assembly. N-methylpyrrolidonedimethyl sulfoxide solvent mixture was used in the acylation (coupling) step.

The solvent mixture used in the acylation step results in a peptidylresin having a swollen volume 1.5 to 2x that of resin solvated by the conventional solvents.

The typical reaction protocol for each cycle of amino-acid incorporation involved: N-alpha deprotection with trifluoracetic acid, washing, neutralization with N,N-diisopropylethylamine, washing, amino-acid incorporation, washing, acetylation, and washing. The pre-activation was accomplished by the dicyclohexylcarbodi-imide mediated formation of the N-hydroxybenzotriazole ester in N-methylpyrrolido. The coupling reaction was initiated in this solvent with the addition of dimethylsulfoxide and N,N-diisopropylethylamine during the reaction period. Following each incorporation step, and prior to capping, a small (5–10 mg.) sample of the peptidyl resin was withdrawn, and subjected to ninhydrin analysis for residual amine. The final peptidyl-resin was analyzed for amino-acid composition. These analytical data provided an estimate of the fidelity of the sequence development, and hence of the desired peptide content of the peptidylresin.

The branched apogenic peptide was released from the resin support by reaction with anhydrous hydrogen fluoride. The branched apogenic peptide was extracted into the medium recommended by Tam, (8M urea, 0.2M Cleland's reagent in 0.1M Tris HCl, pH 8). The solution was dialysized, lyophilized and the amino acid composition analyzed.

The peptides were extracted from the hydrogen fluoride reaction residue with aqueous acetic acid, and, purified by gel filtration chromatography on Sephadex G-50. The amino-acid composition of the isolated products was determined. Purity was greater than 90%.

Finally, the lysine residues of the T-peptides were unmasked by piperidine treatment, and the product was isolated from Sephadex G-50. The cysteine residues of the Beta peptides were retained as the S-acetamidomethyl derivatives. The conjugates were analyzed for amino-acid composition.

The branched apogenic peptide peptides were dissolved in phosphate buffered saline or cell culture medium before use in the cell cultures.

Cell Growth Measurement by MTT Assay

Measurement of cell number as a function of metabolism was determined by the cleavage of 3-(4,5-dimethylthiazol-2-yl)-2,5-diphenyl tetrazolium bromide, (MTT), from Sigma, St. Louis, Mo., dye to formazan crystals. Conversion was measured on a UV MAX plate reader, from Molecular Devices, Palo Alto, Calif. at 570 nm. Data analysis was performed by the Softmax program from Molecular Devices after overnight addition of a cell lysing buffer. The lysing buffer contained 20% w/v of sodium dodecyl sulfate dissolved in a 50% v/v mixture of water and dimethyl formamide, with pH adjusted to 4.7 by 2.5% 1N HCl and 2.5% glacial acetic acid.

Assay for CFU-E and BFU-E Erythroid Progenitors

Susceptibility of erythroid lineage progenitor cells to $C_{Sarma}$VR5-BAP and $A_{Glasgow1}$VR5-BNP was examined by isolation of bone marrow cells from cats, stimulation with erythropoietin and other growth factors while cultured in semi-solid medium. Colony forming units-erythroid or CFR-E are relatively mature erythroid progenitors. Numbers were measured by counting colonies of erythroid cells after four days in culture. Burst forming units-erythroid also referred to herein as "BFU-E" represent an earlier erythroid progenitor cell compared to CFU-E; BFU-E numbers were measured by counting colonies of hemoglobinized erythroid cells after ten days in culture.

To perform the CFU-E and BFU-E assays, bone marrow mononuclear cells ($5\times10^4$ cells/well) were seeded in 12 well plates in duplicate. Briefly, $1.5\times10^5$ bone marrow mononuclear cells in 0.15 ml minimum essential medium alpha modification from GIBCO were added to 1.35 ml of medium containing 1.3% methyl cellulose (Dow-Corning, Midland, Mich.) in Dulbecco's modified minimum essential medium from GIBCO with 0.5% penicillin-streptomycin which, 1% deionized bovine serum albumin (Intergen Co; Purchase, N.Y.), $10^{-4}$M beta mercaptoethanol (Sigma Chemical Co; St. Louis, Mo.), 30% fetal bovine serum (Armour Pharmaceuticals; Kankakee, Ill.), erythropoietin (Terry Fox Labs; Vancouver, BC) at 3 units per ml, and 5% pokeweed mitogen conditioned medium from bone marrow mononuclear cells. Cells and medium were mixed thoroughly and 0.5 ml of cells and medium were added to each of two wells of 12 well culture plates. Cultures were incubated at 37° C. in a humidified atmosphere containing 5% $CO_2$ and 10% $O_2$ in nitrogen enriched air. Erythroid colonies were counted on day 4 of culture as reddish hemoglobinized colonies containing at least 8 cells (CFU-E) and on day 10 as reddish hemoglobinized colonies containing at least 50 cells occurring in multiple subunits (BFU-E).

Assay for CFU-GM:

Susceptibility of granulocytic/monocytic lineage progenitor cells to $C_{Sarma}$VR5-BAP and $A_{Glasgow1}$VR5-BNP was examined by isolation of bone marrow cells from cats, stimulation with pokeweed mitogen conditioned medium followed by culture in semi-solid media. Colony forming units- granulocytic/monocytic or CFU-GM were measured by counting unstained granular colonies after seven days in culture.

To perform the CFU-GM assay, bone marrow mononuclear cells were seeded culture plates in triplicate. Briefly, $2.5\times10^5$ bone marrow mononuclear cells in 0.1 ml minimum essential medium alpha were added to 0.9 ml medium containing 0.5% methylcellulose, 0.4% bovine serum albumin, 2 mM glutamine from GIBCO, 0.5% penicillin-streptomycin, 33% horse serum, from GIBCO, and 11% pokeweed mitogen conditioned medium from bone marrow mononuclear cells. The cells were cultured in 96 well culture plates with $5\times10^4$ cells in 0.2 ml medium per well. Plates were incubated at 37° C. in a humidified atmosphere with 5% $CO_2$ and 10% $O_2$ for 7 days. On the 7th day, colonies containing at least 40 cells were counted as CFU-GM colonies.

Light Microscopy

Eight $\times10^4$ cell in 200 ul of medium were cytocentrifuged at 250 revolutions per minute for 5 minutes on a Cytospin 2 Machine from Shandon, Sewickley, Pa. Cytocentrifuge preparations were stained with Wright-Giemsa.

Electron Microscopy

Cells were harvested, washed in PBS, fixed in 3% glutaraldehyde, and washed in 0.1M cacodylate buffer. The cells were then fixed in 1.3% $OSO_4$, dehydrated in ethanol/propylene oxide, embedded in Epson 812 resin, sectioned and viewed with a Phillips EM300 transmission electron microscope.

All observations and interpretations of morphologic changes were made or verified by board-certified, Diplomates of the American College of Veterinary Pathology (Rojko, Hartke). The presence or absence of morphologic changes ascribable to apoptosis (eg, nuclear and nucleolar clumping, condensation and margination progressing to pyknosis or karyorrhexis and cytoplasmic condensation with or without extensive blebbing and loss of cell surface) was noticed.

DNA Degradation

The occurrence of inter-nucleosomal DNA degradation which appears as DNA strand breaks or DNA laddering, in DNA never exposed to restriction enzymes is definitive biochemical evidence of apoptosis. To determine whether $C_{Sarma}$VR5-BAp induced DNA Strand breaks compatible with apoptosis, DNA was extracted from treated and control cells and electrophorized on agarose gels as follows:

The DNA was prepared as described by Seamus et. al., 1990, by lysing $2\times10^6$ cells in a 10 mM EDTA/50 mM TRIS solution at pH 8.0 with sarkosyl and proteinase K and extracting the DNA with phenol/chloroform.

Briefly, replicates of $2\times10^6$ cells were pelleted, washed at 4° C., resuspended in 200 μL 10 mM EDTA, 50 mM Tris-HCL with 0.5% (w/v) sodium lauryl sarkosinate and 0.5 mg/ml proteinase K, and incubated at 50° C. for 1 hour and with 0.5 mg/ml RNAse A for 1 hour. Samples were heated to 70° C., electrophoresed on 2% agarose gels with 0.1 µg/ml ethidium bromide in 2 mM EDTA/800 mM Tris-phosphate, and photographed with Polaroid 667 film.

Effect of Individual Peptide Chain On Cell Growth

Single chain peptides were added to a feline T4/T8 thymic lymphoma cell line, 3201 cell cultures to examine the ability of the peptides to produce apoptosis. The five peptides were $C_{Sarma}VR5$, $A_{Glasgow1}VR5$, I26, CVR1 and AVR1. Peptides were added to cultures at a concentration of 3.0 µM. Live/dead cell counts using a hemocytometer and trypan blue dye exclusion were taken over five days.

Cell viability did not decrease below 92% in any of the cultures, and were not significantly different from cultures that were not exposed to any peptides.

Evaluation of $C_{Sarma}VR5$-BAP on Cell Growth 3201 Cell Cultures 3201 cells are feline T4/T8-thymic lymphoma cells. Uninfected 3201 cells, FeLV-$A_{Glasgow1}$-infected 3201 cells and FeLV-$C_{Sarma}$-infected 3201 cells were exposed to $C_{Sarma}VR5$-BAP at 5 concentrations: 0.17 µM; 0.35 µM; 0.7 µM; 1.3 µM; and 2.7 µM. $A_{Glasgow1}VR5$-BAP at 2.7 µM was added to separate cell cultures for comparison. The cells were examined daily for 5 days.

Figure 1A:
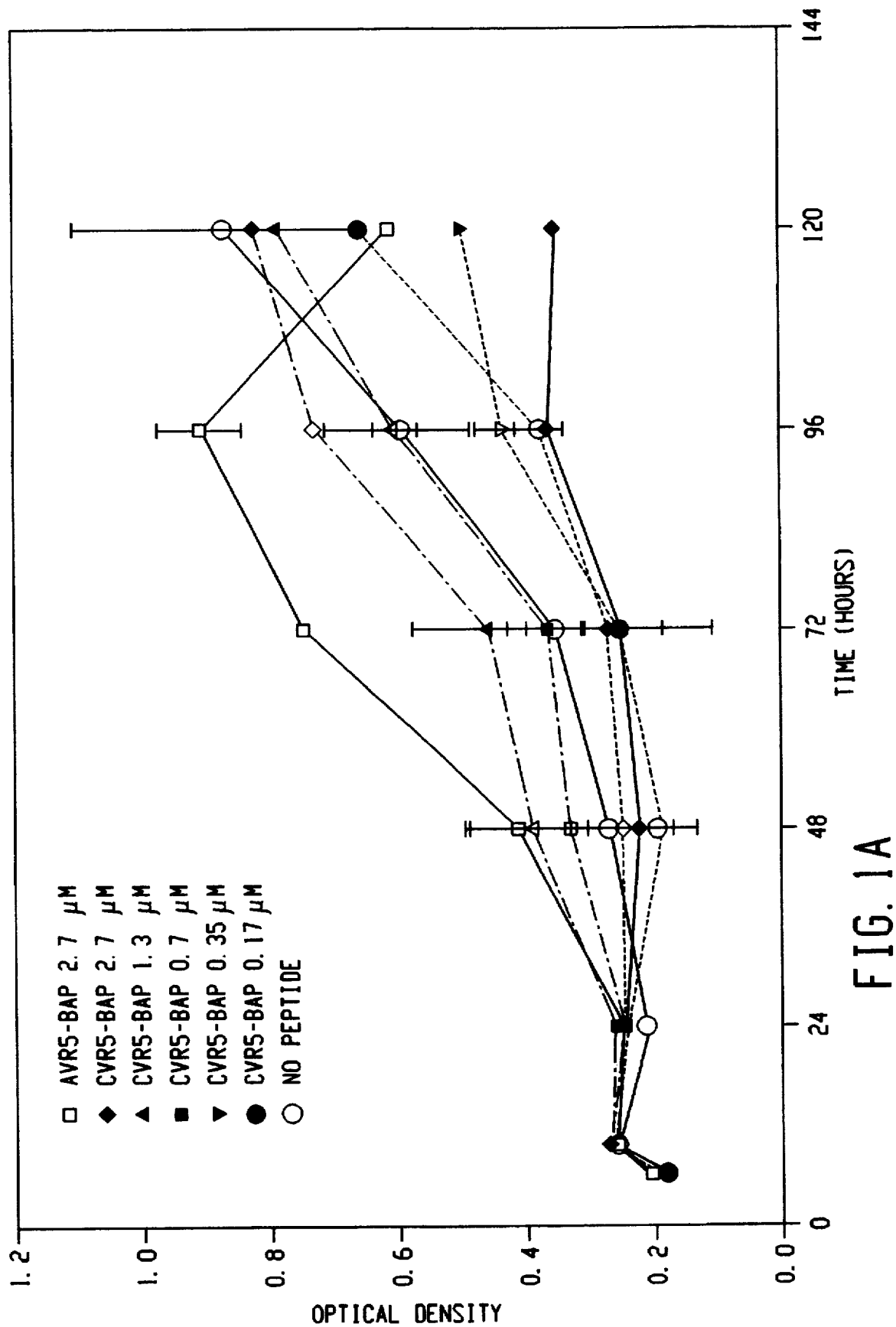
Figure 1B:
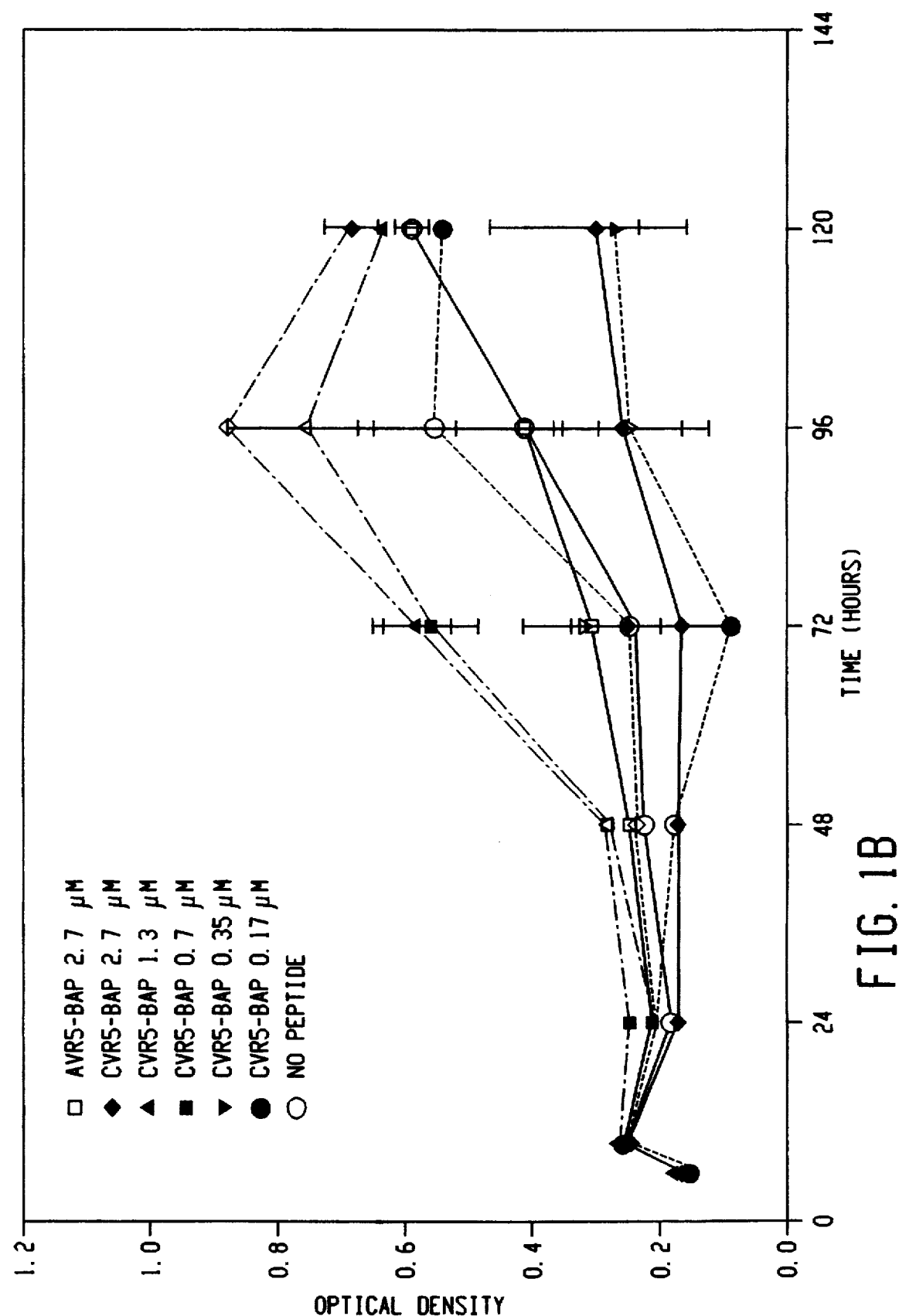
Figure 1C:
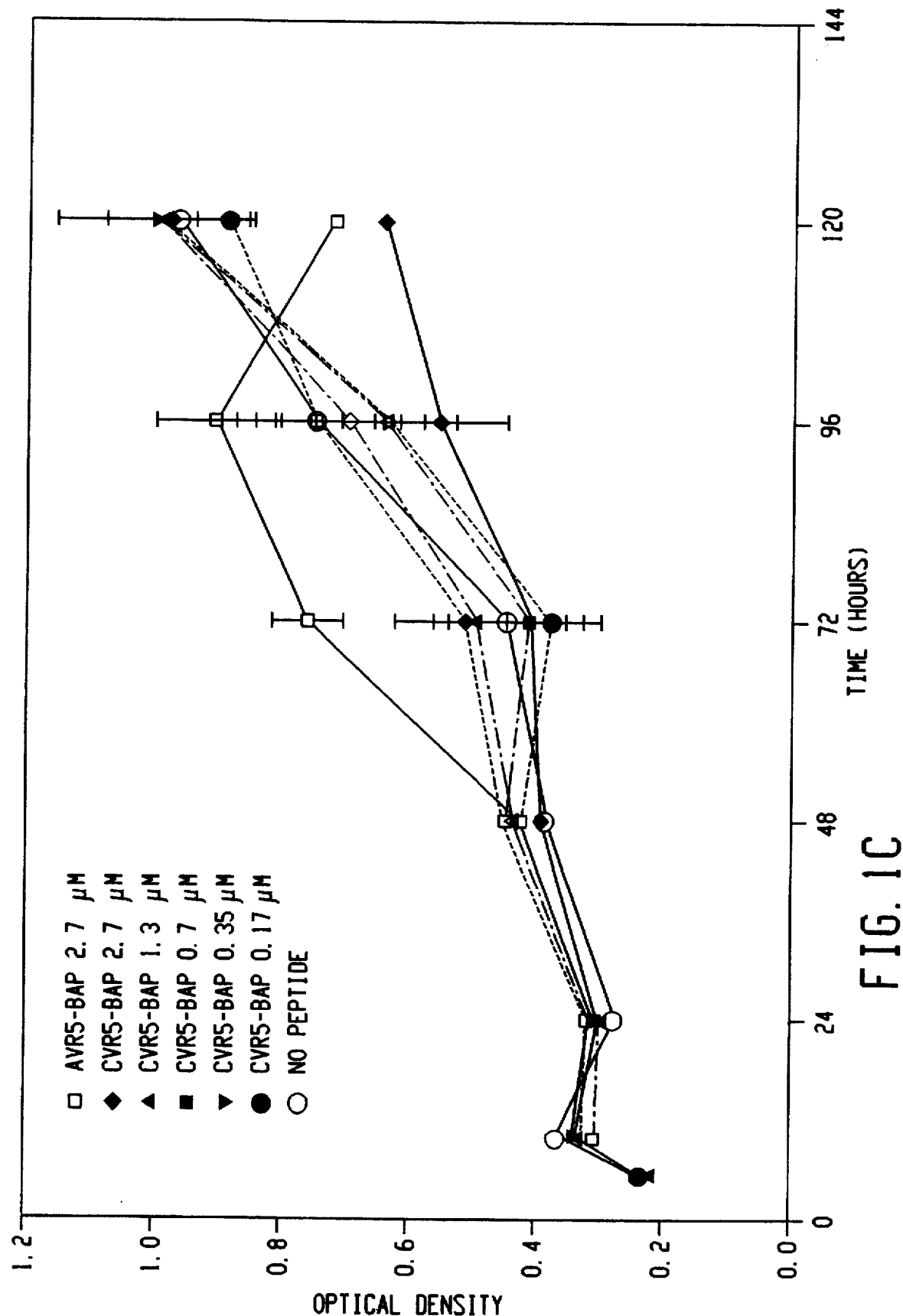

As shown in FIGS. 1A, 1B, and 1C, the growth of uninfected 3201 cells FeLV-$A_{Glasow1}$ infected cells and FeLV-$C_{Sarma}$-infected cells was suppressed by day 5 by 2.7 µM $C_{Sarma}VR5$-BAP. The response was dose dependent; the growth of cells receiving 0.17 µM $C_{Sarma}VR5$-BAP was indistinguishable from control cells. 3201 cells exposed to $A_{Glasgow1}$-BNP at 2.7 µM were unaffected.

Electron microscopic examination of untreated uninfected 3201 cells revealed a fine chromatin pattern with a single central nucleolus, moderately abundant cytoplasm and few cytoplasmic organelles. After exposure to 6 µM $C_{Sarma}VR5$-BAP for 3 days, the cells showed margination and coarse clumping of chromatin with progression to nuclear condensation.

Antibodies were raised in sheep against $C_{Sarma}VR5$-BAP, $A_{Glasgow1}VR5$-BNP, and I26-BAP. These antibodies were examined for their ability to inhibit $C_{Sarma}VR5$-BAP apoptosis in 3201 cells. Sheep serum was heat-treated at 56° C. for 30 minutes, and added at 2.5% (v/v) to 3201 cells cultures containing 2.5% (v/v) fetal bovine serum. $C_{Sarma}VR5$-BAP peptide was added to the culture at a 3 µM concentration.

The $C_{Sarma}VR5$-BAP immunized sheep serum reversed the cell killing by 15% as measured by the MTT assay ($p<0.05$). The anti-$A_{Glasgow1}VR5$-BAP and anti-I26-BAP antibodies raised in sheep had no effect.

3201 cultures were exposed to either 2.84 µM $C_{Sarma}VR5$-BAP alone, or 2.84 µM $C_{Sarma}VR5$-BAP with either 30 µM or 60 µM CVR5, either 30 µM or 60 µM $A_{Glasgow1}VR5$. The cultures were examined daily for five days.

$C_{Sarma}VR5$-BAP induced apoptosis by 20 hours. The CVR5 and AVR5 did not have any inhibitory effect on the apoptosis induced by $C_{Sarma}VR5$-BAP.

HL60 Cell Cultures

HL60 is a human hemolymphatic cell line, specifically a promyelocytic leukemia cell line.

HL60 cell cultures were treated with either 0.5, 1.0, 1.9, 3.8, 7.5 15 or 30 µM $C_{Sarma}VR5$-BAP. Controls received either no polypeptide or 15 µM AVR1-BAP, 15 µM I26-BAP, or 15 µM $A_{Glasgow1}VR5$-BNP. Cell growth was determined at days 1 through 5.

Figure 2:
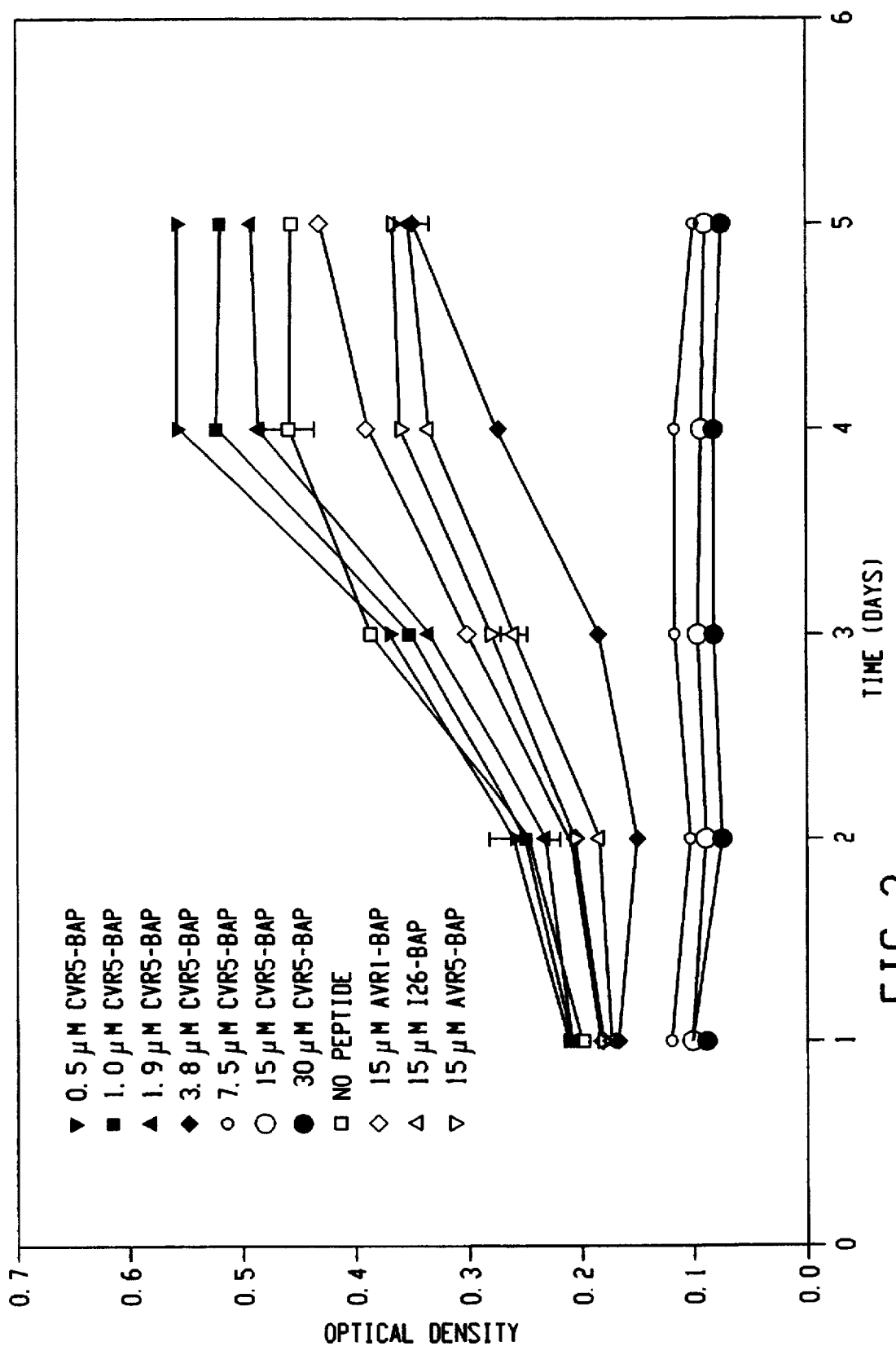

As shown in FIG. 2, the growth of HL60 cells was significantly decreased by addition of 3.8 µM $C_{Sarma}VR5$-BAP beginning at day 1 and continuing through to day 5. Total growth cessation of growth occurred by addition of greater than 7.5 µM $C_{Sarma}VR5$-BAP. The addition of 15 µM AVR1-BAP, I26-BAP, or $A_{Glasgow1}VR5$-BNP had no effect.

In a separate experiment, HL60 cell cultures were treated with 6 µM concentration of $C_{Sarma}VR5$-BAP for 60, 120, and 180 minutes and harvested. Control cell cultures received no $C_{Sarma}VR5$-BAP. The cells were cytocentrifuged, and were examined by light microscopy.

Control cells not treated with $C_{Sarma}VR5$-BAP had large round nuclei with finely clumped chromatin, multiple prominent nucleoli, and a moderate amount of cytoplasm with occasional clear vacuoles. After 1 hour exposure to 6 µM $C_{Sarma}VR5$-BAP, the chromatin began to form coarse granules, and the cytoplasm was decreased in size and more basophilic. After 2 hours, the chromatin began to clump coarsely and marginate, with occasional pyknosis and karyorrhexis. The cytoplasm was condensed, with numerous clear vacuoles. At 3 hours, many HL60 nuclei were pyknotic.

Electron microscopy of untreated HL60 cells revealed large convoluted nuclei, with multiple nucleoli and a finely granular chromatin. The cytoplasm contained occasional mitochondria and lipid vacuoles. After 2 hours exposure to $C_{Sarma}VR5$-BAP, the chromatin was coarsely clumped and marginated. Nucleoli were still present although condensed. The cytoplasm was increased in density with degeneration of cytoplasmic organelles and formation of myelin bodies. There was moderate blebbing of the cytoplasm.

In a separate experiment, HL60 cell cultures were treated with 3.0 or 6.0 µM $C_{Sarma}VR5$-BAP for 2.0, 4.0, 24, 48, and 72 hours. Cells were harvested, the DNA extracted and electrophoresed. Cell viability was also measured and is shown in Table II.

Apoptosis in HL60 cells exposed to $C_{Sarma}VR5$-BAP was demonstrated after 4.0 hours. $C_{Sarma}VR5$-BAP treated cells exhibited regular bands, that is laddering of DNA demonstrating the active cleavage of cellular DNA. Such cleavage is an irreversible step in cell death. The regular bands are produced when the cellular endonucleases cut the DNA at multiples of the internucleosomal distance. Control cells and cells exposed to $A_{Glasgow1}VR5$-BNP, did not exhibit such banding. HL60 cells exposed to 3 µM $C_{Sarma}VR5$-BAP for 24 and 48 hours also exhibited banding of DNA.

HL60 cells were exposed to 30, 60 or 600 µM $C_{Sarma}VR5$ with and without 6 µM CVR5-BAP. The cultures were examined at 4, 20, and 48 hours.

The CVR5 had no cytopathic effect and did not abrogate the effects of the $C_{Sarma}VR5$-BAP in this competitive assay.

H9 Cell Cultures

H9 is a human T4-lymphoblastoid cell line. H9 cell cultures were treated with either 0.5, 1.0, 1.9, 3.8, 7.5 15 or 30 µM $C_{Sarma}VR5$-BAP. Controls received either no polypeptide or 15 µM $A_{Glasgow1}$VR1-BAP, 15 µM I26-BAP, or 15 µM $A_{Glasgow1}VR5$-BNP. Cell growth was determined at days 1 through 5.

Figure 3:
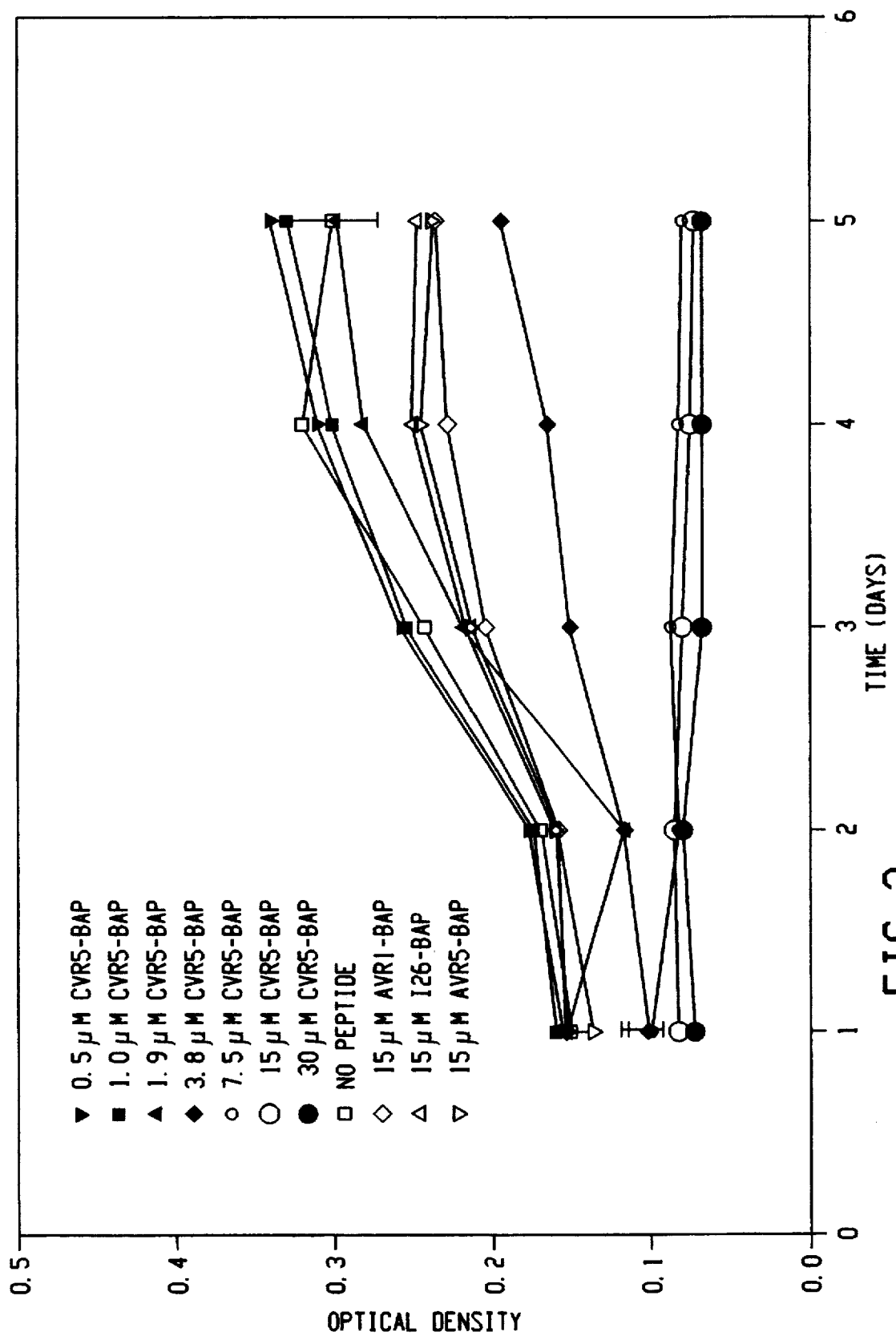

As shown in FIG. 3, the growth of H9 cells was decreased by addition of 3.8 µM $C_{Sarma}VR5$-BAP from day 1 to day 5 and growth cessation occurred by addition of $C_{Sarma}VR5$-BAP above 7.5 µM.

In a separate experiment, H9 cell cultures were treated with 6 µM concentration of $C_{Sarma}VR5$-BAP for 60, 120, and 180 minutes then harvested. The cells were cytocentrifuged, and were examined by light microscopy. Control cultures received no $C_{Sarma}$-BAP.

Control cells not treated with $C_{Sarma}$VR5-BAP had large round nuclei with finely clumped chromatin, multiple prominent nucleoli, and a moderate amount of cytoplasm with occasional clear vacuoles. After 1 hour with 6 µM $C_{Sarma}$VR5-BAP, the chromatin began to form coarse granules and the cytoplasm was condensed. After 2 hours, the chromatin was marginated and clumped and the cytoplasm was condensed. At 3 hours, many nuclei were pyknotic.

Three flasks of HL60 cells and three flasks of H9 cells were seeded with 10 ml of RPMI 1640 containing 10% fetal bovine serum with $5 \times 10^5$ cells per ml. The first flask of each cell line served as the control flask, with no peptide added. The second flask contained 250 µl of 120 µM $A_{Glasgow1}$VR5-BNP for a final concentration of 3.0 µM $A_{Glasgow1}$VR5-BNP. The third flask contained 250 µl of 120 µM $C_{Sarma}$VR5-BAP for a final concentration of 3.0 µM $C_{Sarma}$VR5-BAP. At 4 hours, 24 hours, 48 hours and 72 hours post exposure, cells were counted using trypan blue stain and $2 \times 10^6$ cells were removed and the DNA prepared for examination. Cell viability was measured and is shown in Table II.

Apoptosis was demonstrated after 48 hours in H9 cells exposed to $C_{Sarma}$VR5-BAP. $C_{Sarma}$VR5-BAP treated cells exhibited regular bands of DNA demonstrating the active cleavage of cellular DNA. Such cleavage is an irreversible step in cell death. The regular bands are produced when the cellular endonucleases cut the DNA at multiples of the internucleosomal distance. Control cells and cells exposed to $A_{Glasgow1}$VR5-BNP, did not exhibit such banding.

K562 Cell Cultures

K562 is a pluripotent human leukemia stem cell line. K562 cell cultures were treated with either 0.5, 1.0, 1.9, 3.8, 7.5 15 or 30 µM $C_{Sarma}$VR5-BAP. Controls received either no polypeptide or 15 µM $A_{Glasgow1}$VR1-BAP, 15 µM I26-BAP, or 15 µM $A_{Glasgow1}$VR5-BNP. Cell growth was determined at days 1 through 5.

Figure 4:
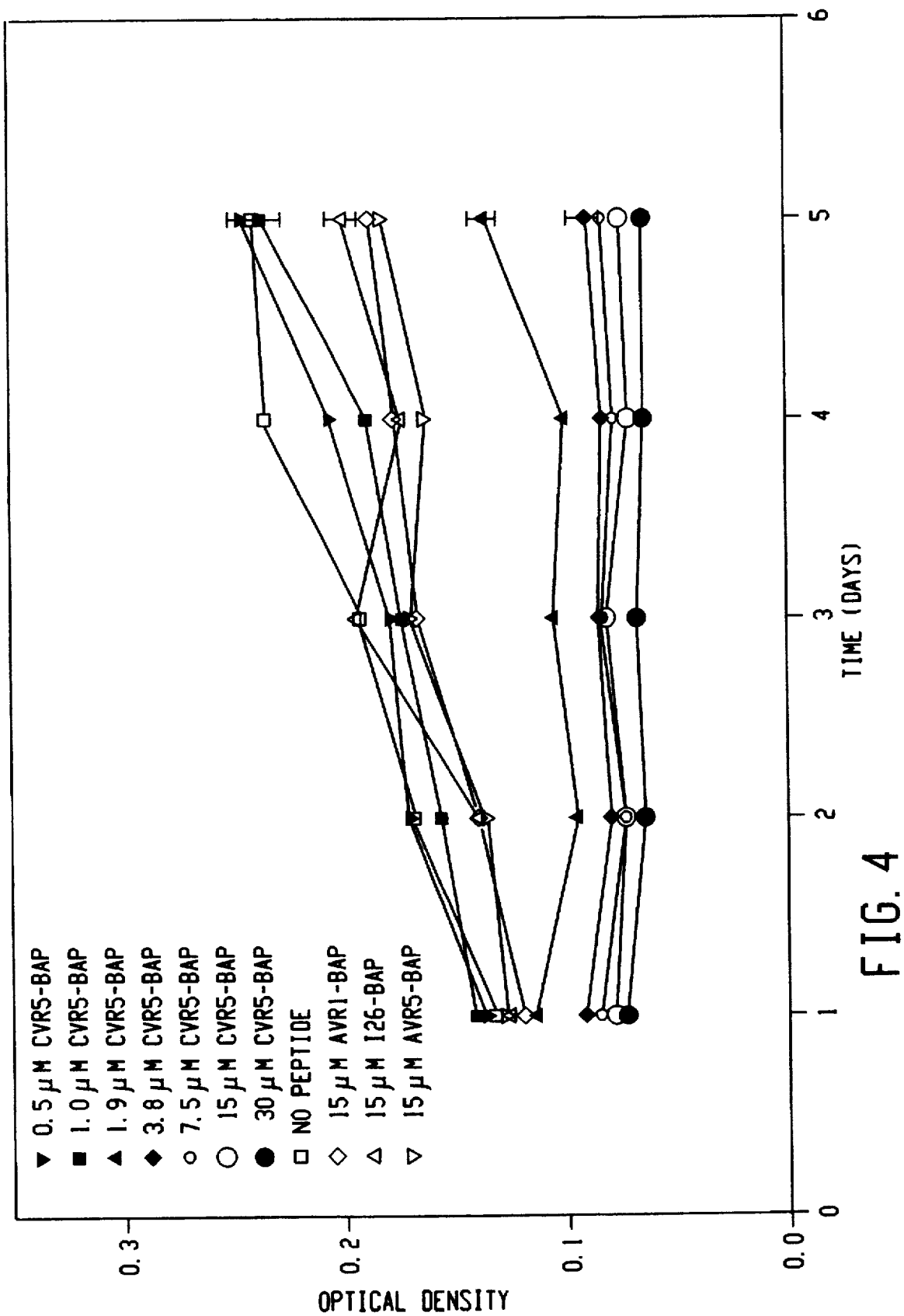

As shown in FIG. 4, the growth of K652 cells was suppressed by 1.9 µM $C_{Sarma}$VR5-BAP from day 1 to day 5.

In a separate experiment, K562 cell cultures were treated with 6 µM concentration of $C_{Sarma}$VR5-BAP for 2, 4, and 10 hours, then harvested. The cells were cytocentrifuged, and were examined by light microscopy. Control cell cultures received no $C_{Sarma}$VR5-BAP.

The control K562 cells not treated with $C_{Sarma}$VR5-BAP had large multiple nuclei with multiple prominent nucleoli and moderate cytoplasmic vacuolization. At 2 hours, cells treated with $C_{Sarma}$VR5-BAP displayed minimal nuclear and cytoplasmic changes; that is minimal chromatic clumping and cytoplasmic condensation. At four hours, $C_{Sarma}$VR5-BAP treated cells had deep basophilic structures interpreted as pyknotic nuclei and condensed cytoplasm. At 10 hours, the changes in the $C_{Sarma}$VR5-BAP treated cells were even more prominent. In comparison, after 10 hours, cells treated with $A_{Glasgow1}$VR5-BAP were indistinguishable from untreated control cells.

F422 Cell Cultures

F422 is a FeLV-infected feline lymphoblastoid cell line. F422 cells were treated with 6 µM, 12 µM, or 24 µM $C_{Sarma}$VR5-BAP. Control cell cultures received either no peptide or 24 µM $A_{Glasgow1}$VR5-BAP. Cell growth was determined at 2 days and 4 days post exposure.

Figure 5:
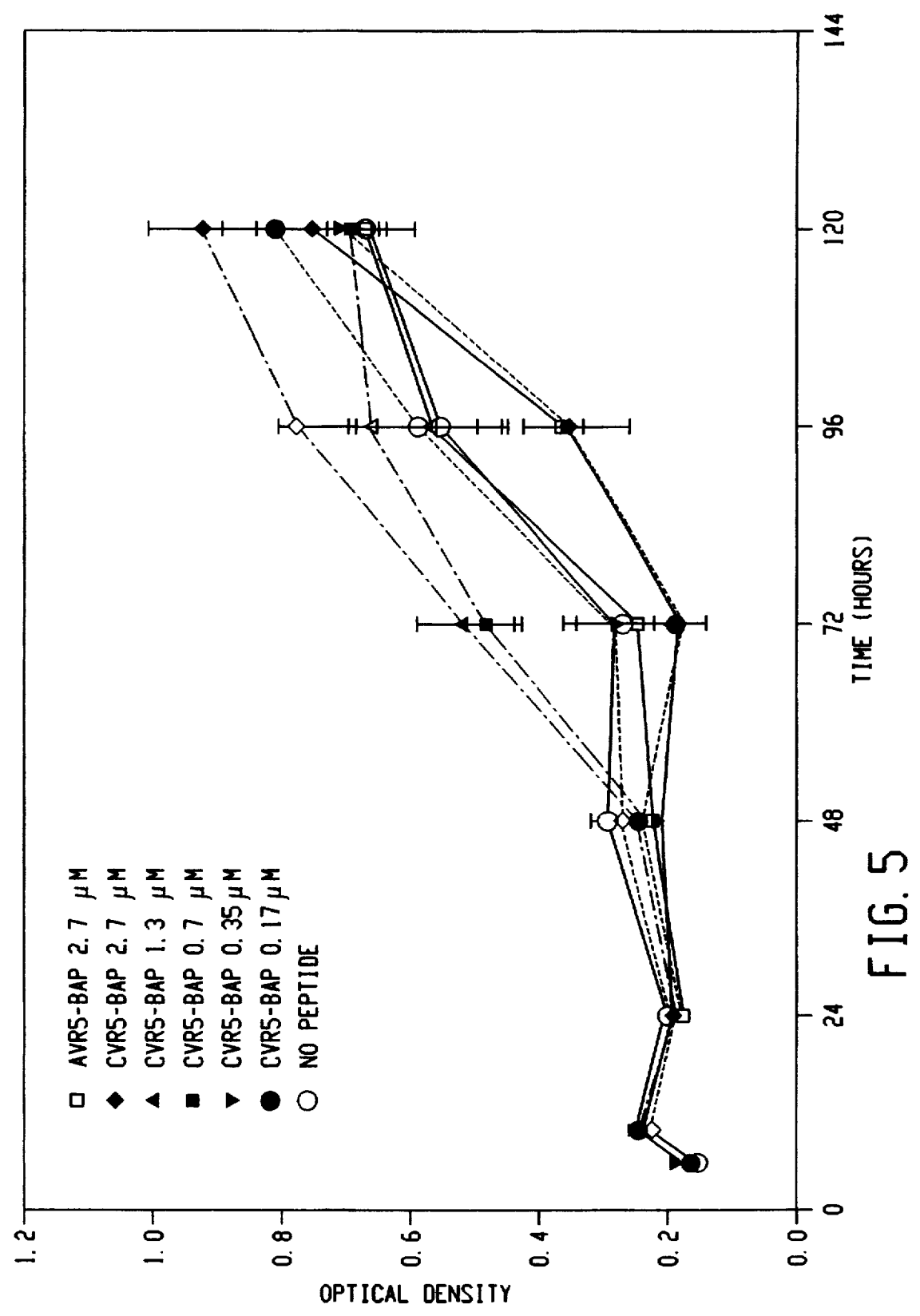

As shown in FIG. 5, growth of the F422 cells was suppressed by addition of $C_{Sarma}$VR5-BAP at 12 µM or higher concentrations the $A_{Glasgow1}$VR5-BNP did not suppress growth even at 24 µM concentrations.

MCC Cell Cultures

MCC is a feline large granular lymphoma cell line. MCC cell cultures were treated with 0.17, 0.35, 0.7, 1.3, and 2.7 µM $C_{Sarma}$VR5-BAP or 2.7 µM $A_{Glasgow1}$VR5-BNP or no peptide. Cell growth was determined at various time points up to 120 hours.

MCC cells did not exhibit any growth suppression from $C_{Sarma}$VR5-BAP or $A_{Glasgow1}$VR5-BNP.

In a second experiment, MCC cells were treated with 6, 12, or 24 µM $C_{Sarma}$VR5-BAP. Control cell cultures received either no peptide or 6, 12, or 24 µM $C_{Sarma}$VR5-BAP. Cell growth was determined at 2 and 4 days post exposure.

Figure 6:
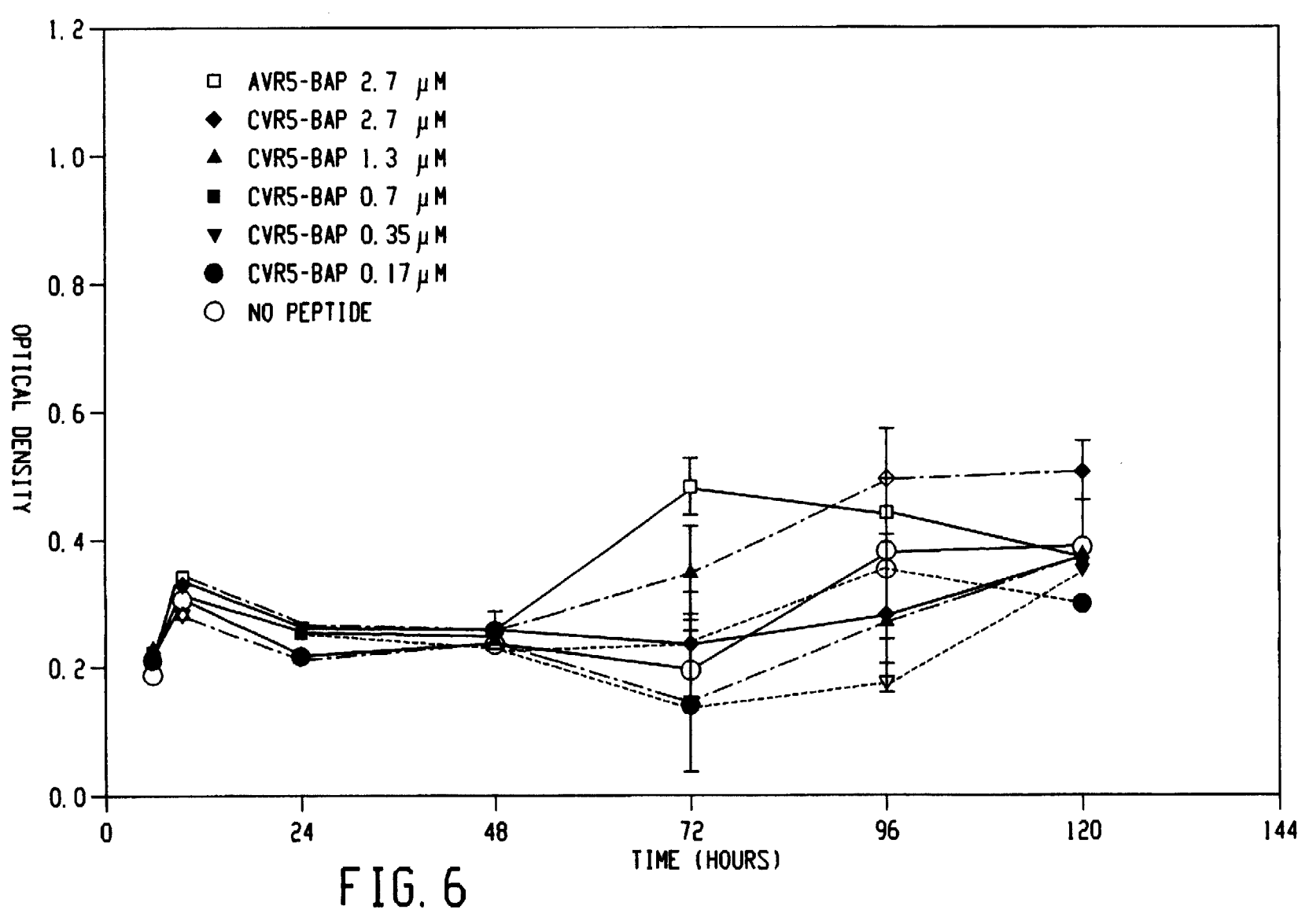

As shown in FIG. 6, growth of the MCC cells was suppressed by addition of $C_{Sarma}$VR5-BAP at 12 µM and higher. $A_{Glasgow1}$VR5-BAP, did not suppress growth.

Clone 81 Cell Cultures

Clone 81 is a feline fibroblastoid cell line. Clone 81 cell cultures were treated with either 0.17, 0.35, 0.7, 1.3 or 2.7 µM $C_{Sarma}$VR5-BAP. Control cell cultures received either no peptide or 2.7 µM $A_{Glasgow1}$VR5-BNP. Cell growth was determined at various time points up to 120 hours.

The growth of clone 81 cells was not affected by 2.7 µM $C_{Sarma}$VR5-BAP. Other work, not shown, showed that apoptosis was not induced in clone 81 with 100 µM $C_{Sarma}$VR5-BAP which is more than ten times higher than the dosage that induced apoptosis in other cell lines.

FEA Cell Cultures

FEA is a feline fibroblastoid cell line. FEA-FeLV-$A_{Glasgow1}$ are FEA cells infected with FeLV-$A_{Glasgow1}$. FEA-FeLV-$A_{Glasgow1}$ cultures were treated with either 0.17, 0.35, 0.7, 1.3 or 2.7 µM in one experiment, and 1.25, 2.5 20 µM $C_{Sarma}$CVR5-BAP in a second experiment. Control cell cultures received either no peptide or 2.7 µM $A_{Glasgow1}$VR5-BNP. Cell growth was determined at 1 to 5 days post exposure.

The growth of FEA-FeLV-$A_{Glasgow1}$ was not affected by $C_{Sarma}$VR5-BAP at concentrations up to 20 µM.

HT1080 Cell Cultures

HT1080 is a human fibroblastoid cell line. HT1080 cultures were treated with either 0.17, 0.35, 0.7, 1.3 or 2.7 µM $C_{Sarma}$VR5-BAP. Control cell cultures received either no peptide or 2.7 µM $A_{Glasgow1}$VR5-BNP. Cell growth was determined at 1 to 5 days post exposure.

Growth of HT1080 cells was not decreased by addition of $C_{Sarma}$VR5-BAP at 2.7 µM, but was enhanced with the addition 2.7 µM $A_{Glasgow1}$VR5 after four days.

DH82 Cell Cultures

DH82 is a canine histiocytic lymphoma cell line. DH82 cell cultures were treated with either 0.17, 0.35, 0.7, 1.3 or 2.7 µM $C_{Sarma}$VR5-BAP. Control cell cultures received either no peptide or 2.7 µM $A_{Glasgow1}$VR5-BNP Cell growth was determined at 1 to 5 days post exposure.

Growth of the cells was not affected by the addition of $C_{Sarma}$VR5-BAP or $A_{Glasgow1}$VR5-BAP peptide.

ERIC Cell Cultures

ERIC is a human T4-lymphoblastoid cell line derived from the CEM cell line. ERIC cell cultures were treated with either 0.17, 0.35, 0.7, 1.3 or 2.7 µM $C_{Sarma}$VR5-BAP. Control cell cultures received either no peptide or 2.7 µM $A_{Glasgow1}$VR5-BNP Cell growth was determined at 1 to 5 days post exposure.

Growth of ERIC cells was not affected by the addition of $C_{Sarma}$VR5-BAP or $A_{Glasgow1}$VR5-BAP peptide.

U937 Cell Cultures

U937 is a human histiocytic lymphoma cell line. U937 cell cultures were treated with 0.17, 0.35, 0.7, 1.3 or 2.7 µM $C_{Sarma}$VR5-BAP. Control cell cultures received either no peptide or 2.7 µM $A_{Glasgow1}$VR5-BNP. Cell growth was determined at 1 to 5 days post exposure.

Figure 7:
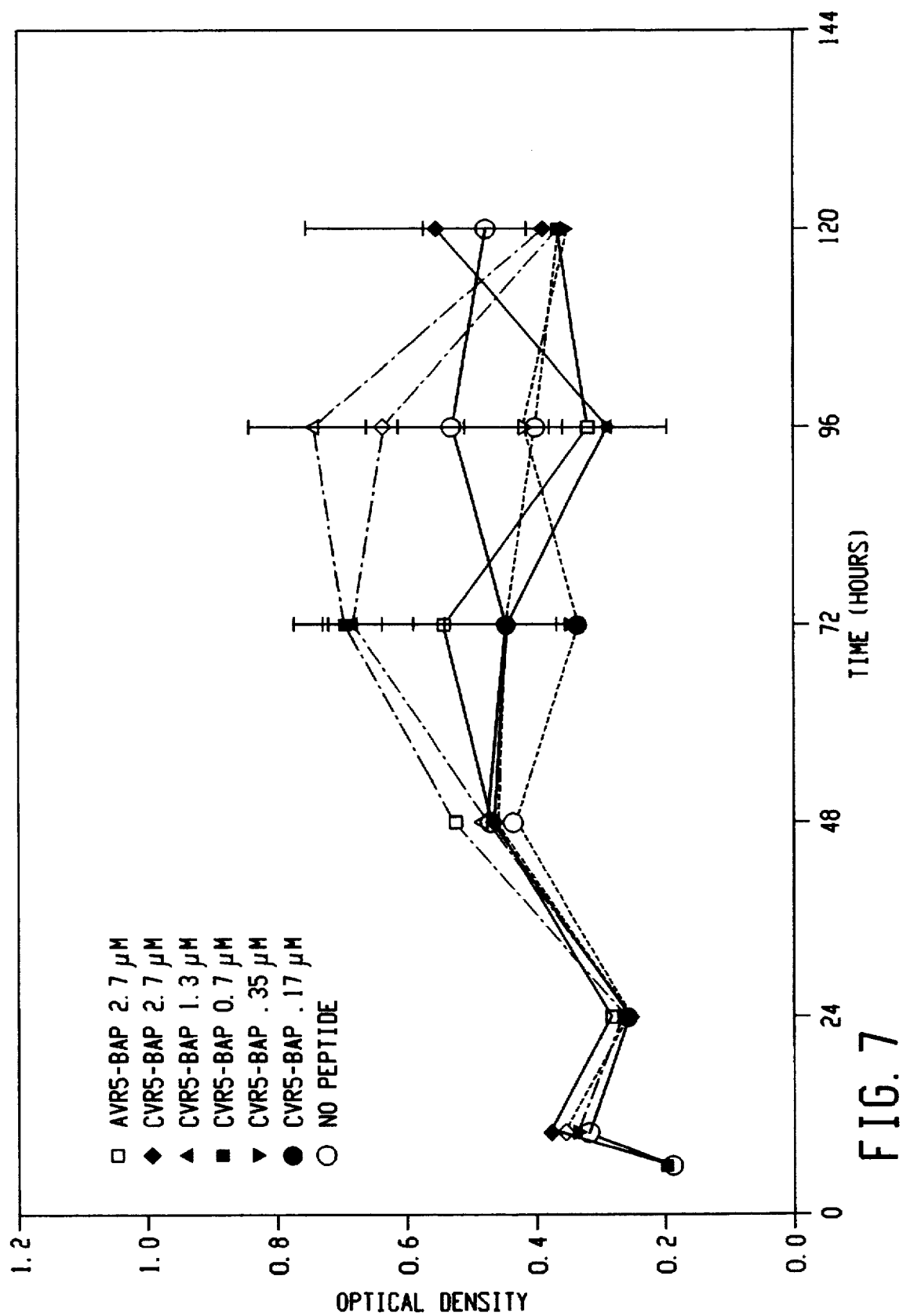

As shown in FIG. 7, the growth of U937 cells was not affected by treatment with 2.7 µM $C_{Sarma}$VR5-BAP.

In a separate to experiment, 6.0 µM concentrations of $C_{Sarma}$VR5-BAP added to U937 cultures was diluted 0.6 µM after 2 hours and suppressed growth.

CFU-E Cell Cultures

Susceptibility of erythroid lineage progenitor cells to $C_{Sarma}$VR5-BAP and $A_{Glasgow1}$VR5-BNP was examined by isolation of bone marrow cells from cats, stimulation with erythropoietin and other growth factors followed by culture in semi-solid media. Colony forming units-erythroid or CFU-E numbers were measured by counting colonies of erythroid cells after four days in culture.

CFU-E cultures were treated with 0.040, 0.40, and 4.0 µM $C_{Sarma}$VR5-BAP. Control cultures received either no peptide or 0.040, 0.40, or 4.0 µM $A_{Glasgow1}$VR5-BAP. Cell colony number was determined at 4 days post exposure.

Figure 8:
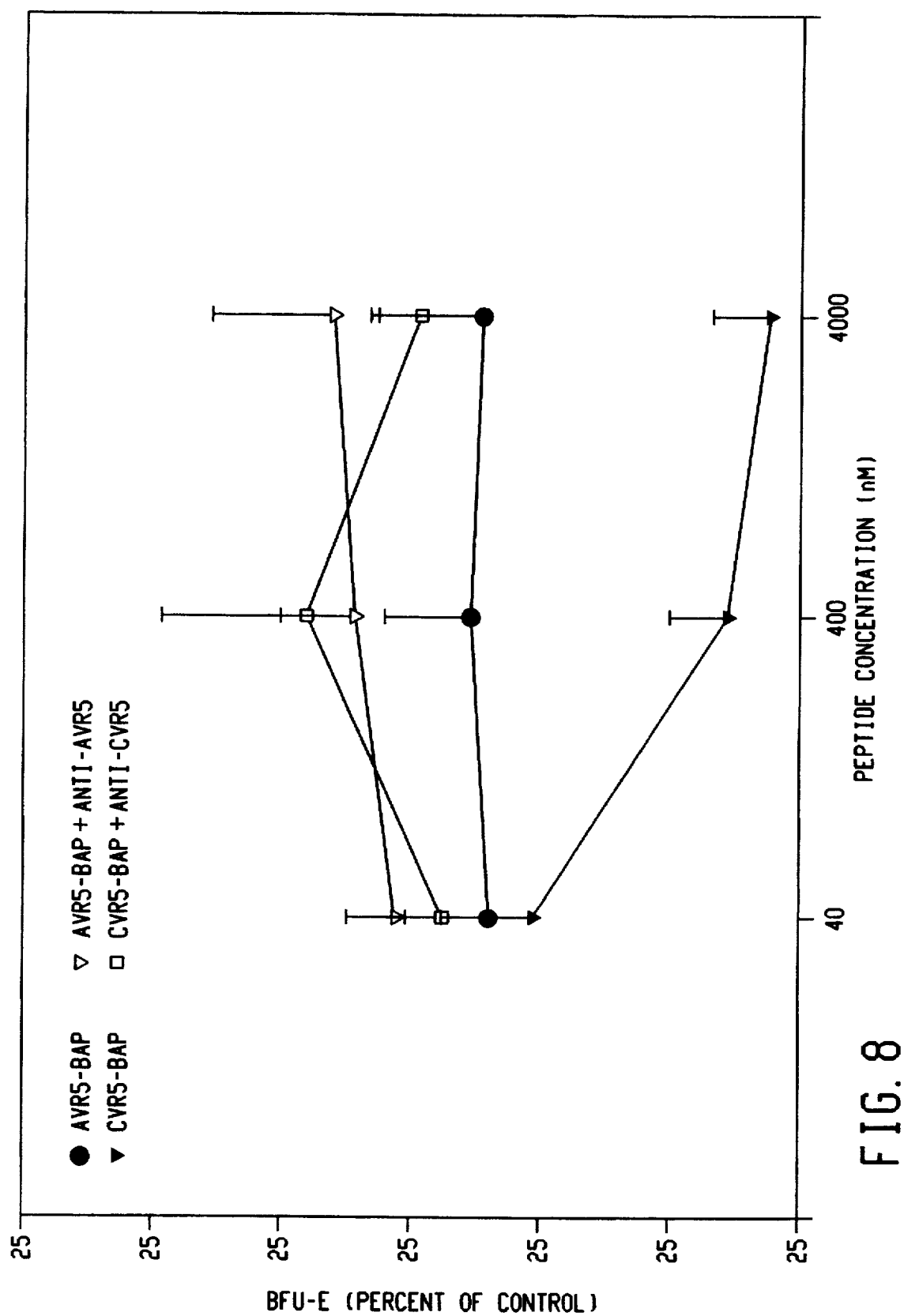
FIG. 8 is a graph showing the effect of $C_{Sarma}$VR5-BAP on CFU-E cells; the circle represents AVR5-BAP; the colored upside down triangle represents CVR5-BAP; the uncolored upside down triangle represents AVR5-BAP+anti-AVR5; and the square represents CVR5-BAP+anti-CVR5.

As shown in FIG. 8, CFU-E cultures were highly sensitive to $C_{Sarma}$VR5-BAP and were reduced to less than 35% of control values by the addition of 0.40 µM to 4.0 µM $C_{Sarma}$VR5-BAP. In comparison, $A_{Glasgow1}$VR5-BAP did not affect CFU-E cultures.

In the same experiment at each dose level of branched apogenic peptide, sheep anti-$C_{Sarma}$VR5-BAP and sheep anti-$A_{Glasgow1}$VR5-BAP antibodies, purified over protein-A and immunoaffinity columns, were added to CFU-E cultures at 0.1 mg/ml.

Sheep anti-$C_{Sarma}$VR5-BAP antibodies abrogated the suppressive effect of $C_{Sarma}$VR5-BAP in CFU-E cultures as shown in FIG. 8.

BFU-E Cell Cultures

Susceptibility of erythroid lineage progenitor cells to $C_{Sarma}$VR5-BAP and $A_{Glasgow1}$VR5-BNP was examined by isolation of bone marrow cells from cats, stimulation with erythropoietin and other growth factors followed by culture in semi-solid media. Burst forming units-erythroid or BFU-E which represents an earlier progenitor cell compared to CFU-E cells were measured by counting colonies of erythroid cells after ten days in culture.

BFU-E cell cultures were treated with 0.040, 0.40, or 4.0 µM $C_{Sarma}$VR5-BAP. Control cultures received either no peptide or 0.040, 0.40, or 4.0 µM $A_{Glasgow1}$VR5-BAP. Cell colony number was determined at 10 days post exposure.

Figure 9:
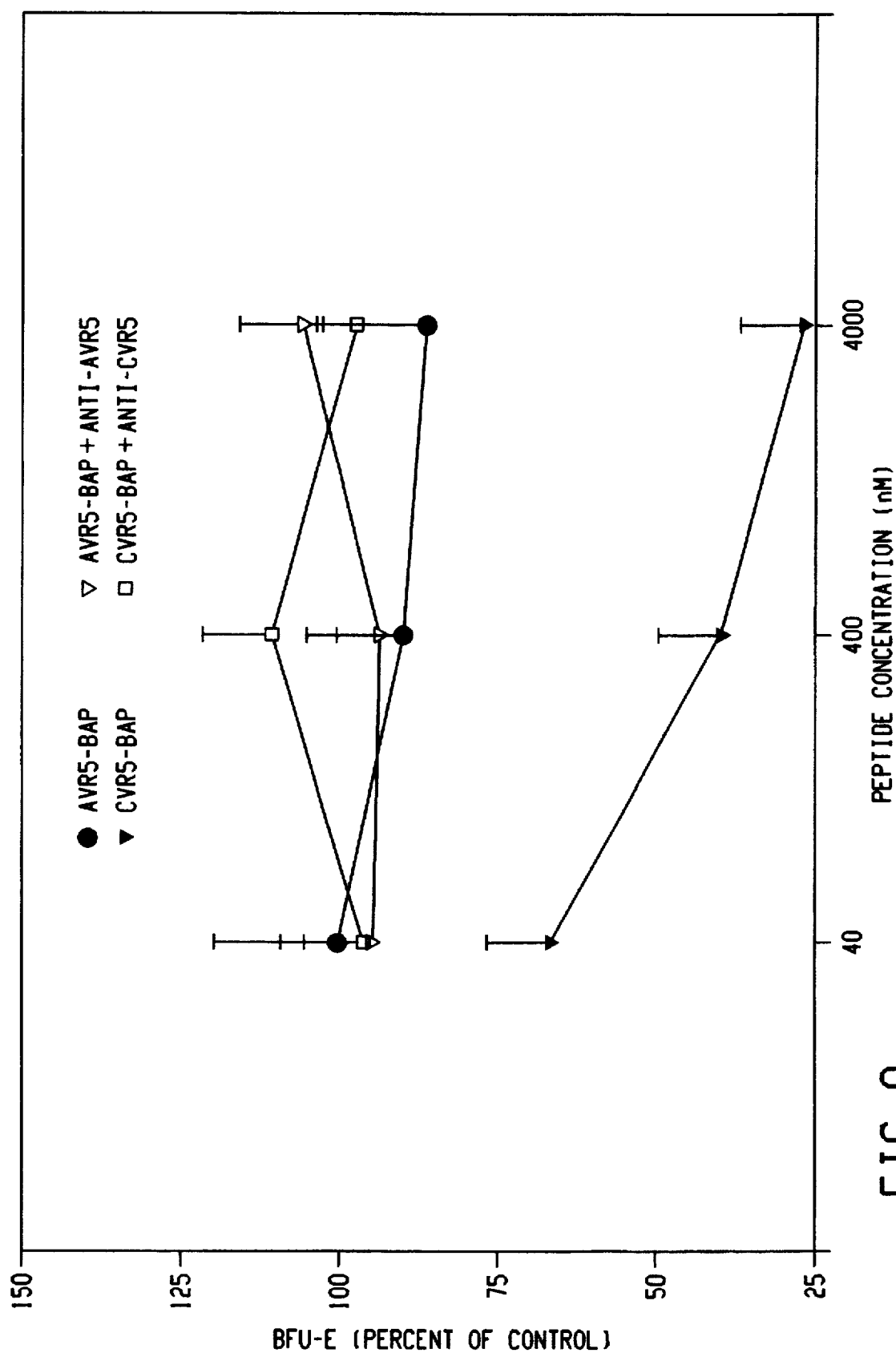
FIG. 9 is a graph showing the effect of $C_{Sarma}$VR5-BAP on BFU-E cells; the circle represents AVR5-BAP; the colored upside down triangle represents CVR5-BAP; the uncolored upside down triangle represents AVR5-BAP+anti-AVR5; and the square represents CVR5-BAP+anti-CVR5.

As shown in FIG. 9, BFU-E cultures were more sensitive than CFU-E cultures. BFU-E cultures were reduced to 62% of untreated culture values by the addition of 0.4 µM $C_{Sarma}$VR5-BAP. In comparison, $A_{Glasgow1}$VR5-BAP did not affect BFU-E cultures.

In the same experiment at each dose level of branched apogenic peptide, sheep anti-$C_{Sarma}$VR5-BAP and sheep anti-$A_{Glasgow1}$VR5-BAP antibodies, purified over protein-A and immunoaffinity columns, were added to BFU-E cultures at 0.1 mg/ml.

Sheep anti-$C_{Sarma}$VR5-BAP antibodies abrogated the suppressive effect of $C_{Sarma}$VR5-BAP in CBU-E cultures as shown in FIG. 9.

CFU-GM Cell Cultures

Susceptibility of granulocytic/monocytic lineage progenitor cells to $C_{Sarma}$VR5-BAP and $A_{Glasgow1}$VR5-BNP was examined by isolation of bone marrow cells from cats, stimulation with pokeweed mitogen conditioned bone marrow or splenic culture medium, followed by culture in semi-solid media. Colony forming units-granulocytic/monocytic or CFU-GM were measured by counting colonies after seven days in culture.

CFU-GM cell cultures received from 0.040, 0.40, and 4.0 µM $C_{Sarma}$VR5-BAP. Control cultures received either no peptide or 0.040, 0.40, and 4.0 µM $A_{Glasgow1}$VR5-BAP. Cell growth was determined 7 days after exposure.

Neither $C_{Sarma}$VR5-BAP or $A_{Glasgow1}$VR5-BAP suppressed the growth of CFU-GM cultures.

El-4 cells

The EL-4 cell line is a transformed cell line that is a thymic lymphoma derived from mouse thymocytes. EL-4 cell cultures were exposed to 0.9, 1.9, 38, 7.5, 15, 30, and 60 µM $C_{Sarma}$VR5-BAP for 24 hours. Control cell cultures did not receive the $C_{Sarma}$VR5-BAP. Cell growth was determined by MTT assay.

Figure 10:
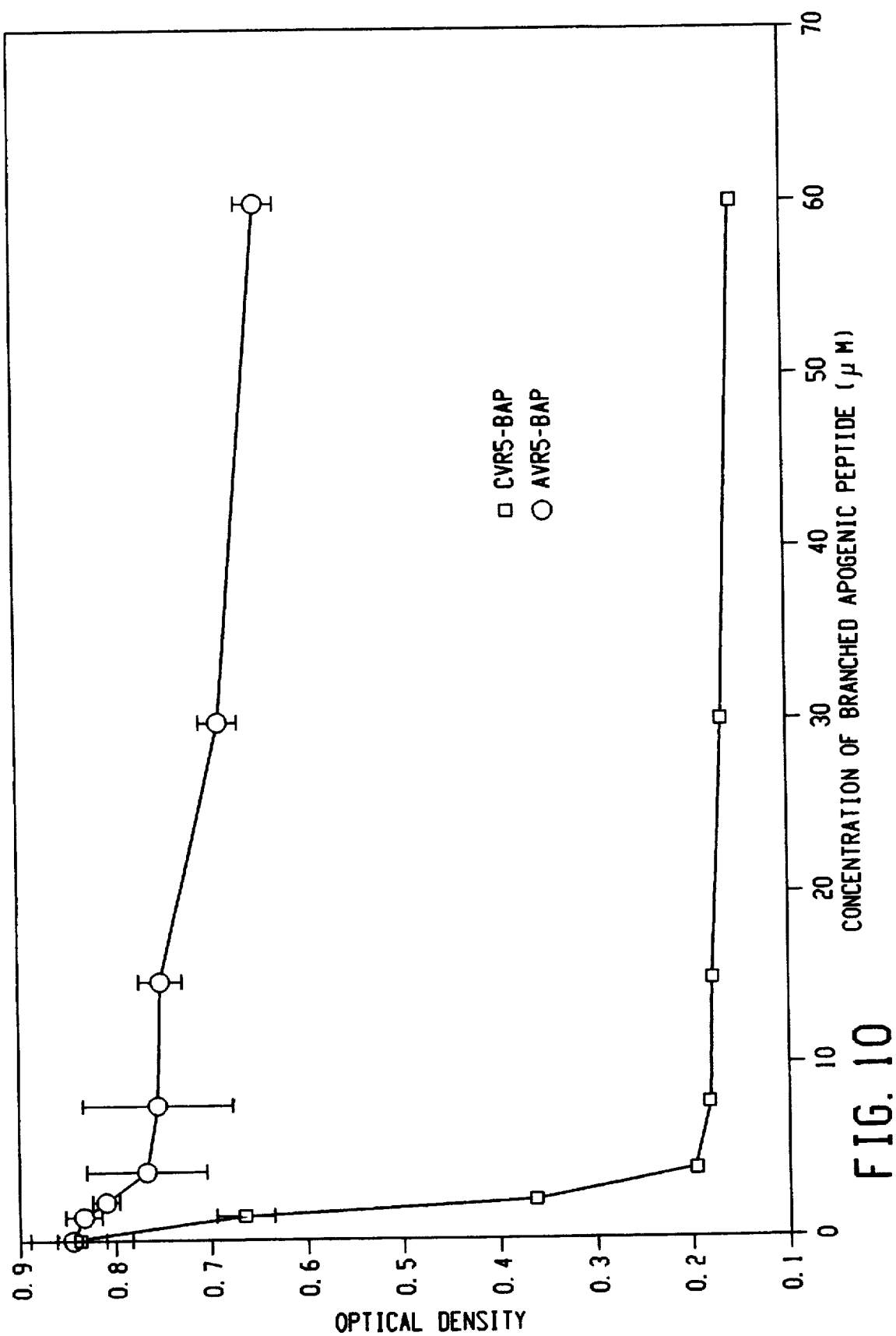
FIG. 10 is a graph showing the effect of $C_{Sarma}$VR5-BAP on EL-4 cells; the square represents CVR5-BAP and the circle represents AVR5-BAP.

As shown in FIG. 10, in cell cultures receiving 1.9 µM $C_{Sarma}$VR5-BAP and higher, the growth was reduced to 44% of untreated cell cultures.

Human Keratinocytes

Human keratinocytes are a primary culture derived from human foreskin epithelium. The keratinocytes were grown in serum-free keratinocyte medium and exposed to 0.7, 1.75, or 3.5 µM of $C_{Sarma}$VR5-BAP for 1, 3, 5, and 7 days. Control cell cultures either received either no branched apogenic peptide or $A_{Glasgow1}$VR5-BNP for comparison. Cell viability and number was measured by the MTT assay.

Figure 11:
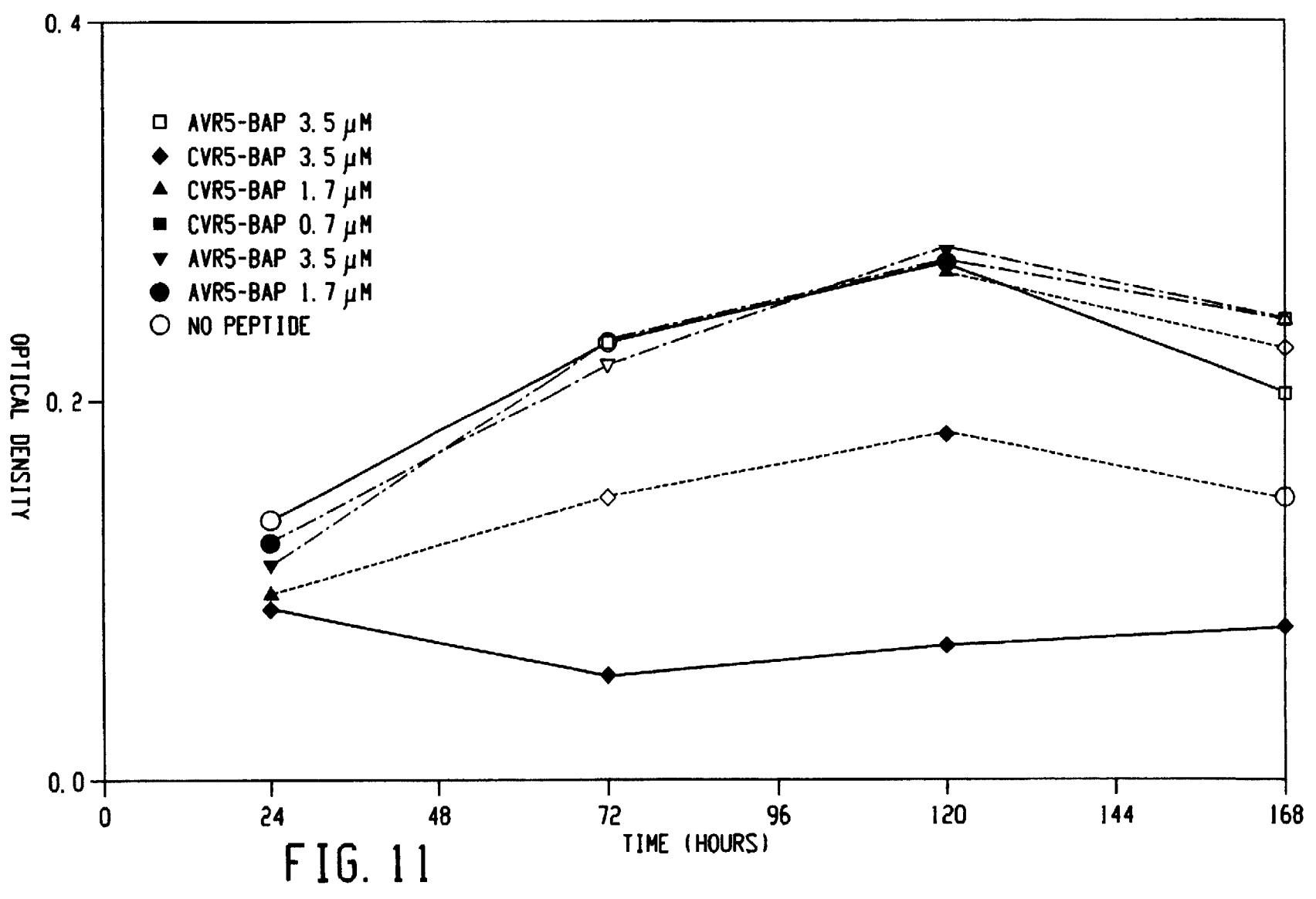

As shown in FIG. 11, by three days after exposure to 1.75 µM $C_{Sarma}$VR5-BAP or higher concentrations, the cell growth dropped to 66% of control cultures, and remained at or below this level for the seven days.

Ciliary Ganglia

The ciliary ganglia are a primary cell culture derived from chicken embryos and grown in Dulbecco's modified minimal essential medium supplemented with 10% fetal calf serum. The ciliary ganglia were exposed to 12 µM $C_{Sarma}$VR5-BAP. Control cultures received either no branched apogenic peptide or 12 µM $A_{Glasgow1}$VR5-BNP for comparison. Viability was determined at 24 hours by phase contrast microscopy.

Cell cultures exposed to $C_{Sarma}$VR5-BAP had significantly decreased viability by 24 hours post exposure. The cells were highly variable in size with vacuolated cytoplasms and degenerate sometimes pyknotic nuclei.

FRTL5 Cells

The FRTL5 cell line is a transformed thyroid carcinoma cell line derived from rat thyroid epithelial cells. Cells were seeded in chamber slides in media supplemented with insulin, thyroid stimulating hormone, glycyl-L-histidyl-lysine, somatostatin; transferrin; and hydrocortisone. The cells were grown for two days, and then divided into two groups, one which continued to receive the supplemented medium, and one group which received only basal medium, which contained Hams F-12, Coons modification with 5% newborn calf serum. After two additional days of incubation, one chamber from each group was exposed to 12 µM $C_{Sarma}$VR5-BAP for 5, 24, or 48 hours. Then the media was removed from the slides, the slides were fixed with methanol, and stained with Wright-Giemsa stain. The slides were evaluated by light microscopy.

The FRTL5 cell cultures in supplemented media which were exposed to $C_{Sarma}$VR5-BAP for 24 hours or longer demonstrated diminished colony size, rounding up of cell borders and decreased cell number compared to unexposed cells. Growth-arrested cells, that is cells grown in basal medium after two days were not significantly different from control cells at any time point.

Resting PBLs Cultures

Feline peripheral blood lymphocytes, hereinafter also designated "PBLs", were isolated from peripheral blood by phycol-hypaque density gradient centrifugation and counted. PBLs were seeded at 1×10⁶ cells per ml in RPMI 1640 with 20% fetal calf serum. $C_{Sarma}$VR5-BAP or $A_{Glasgow1}$VR5-BNP at 6.0 µM concentration was added and samples were assayed by MTT at 0, 4, 18, and 21 hours post-exposure.

Figure 12:
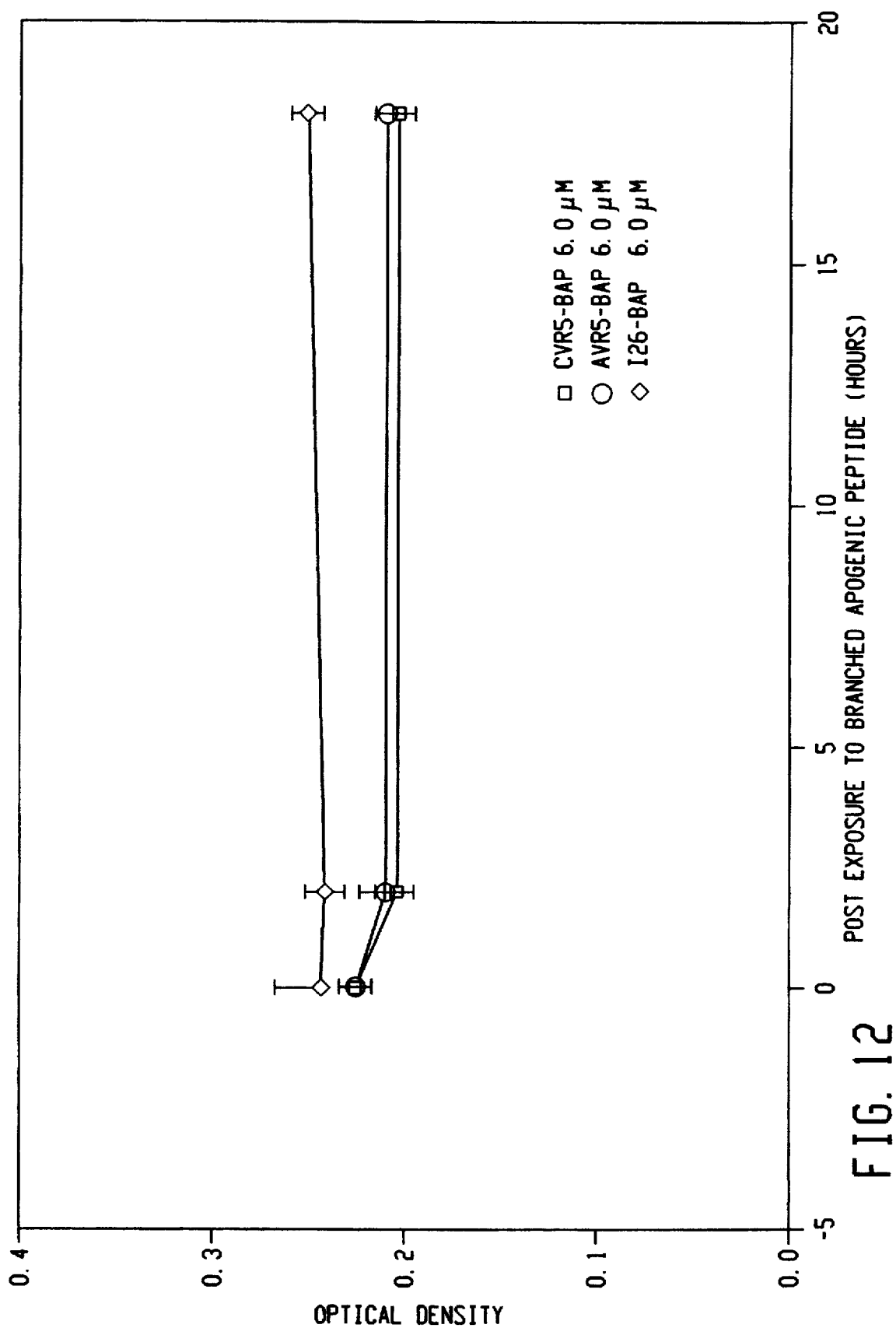
FIG. 12 is a graph showing the effect of $C_{Sarma}$VR5-BAP on resting feline peripheral blood lymphocytes; the square represents CVR5-BAP 6.0 μM; the circle represents AVR5-BAP 6.0 μM; and the diamond represents I26-BAP 6.0 μM.
Figure 13:
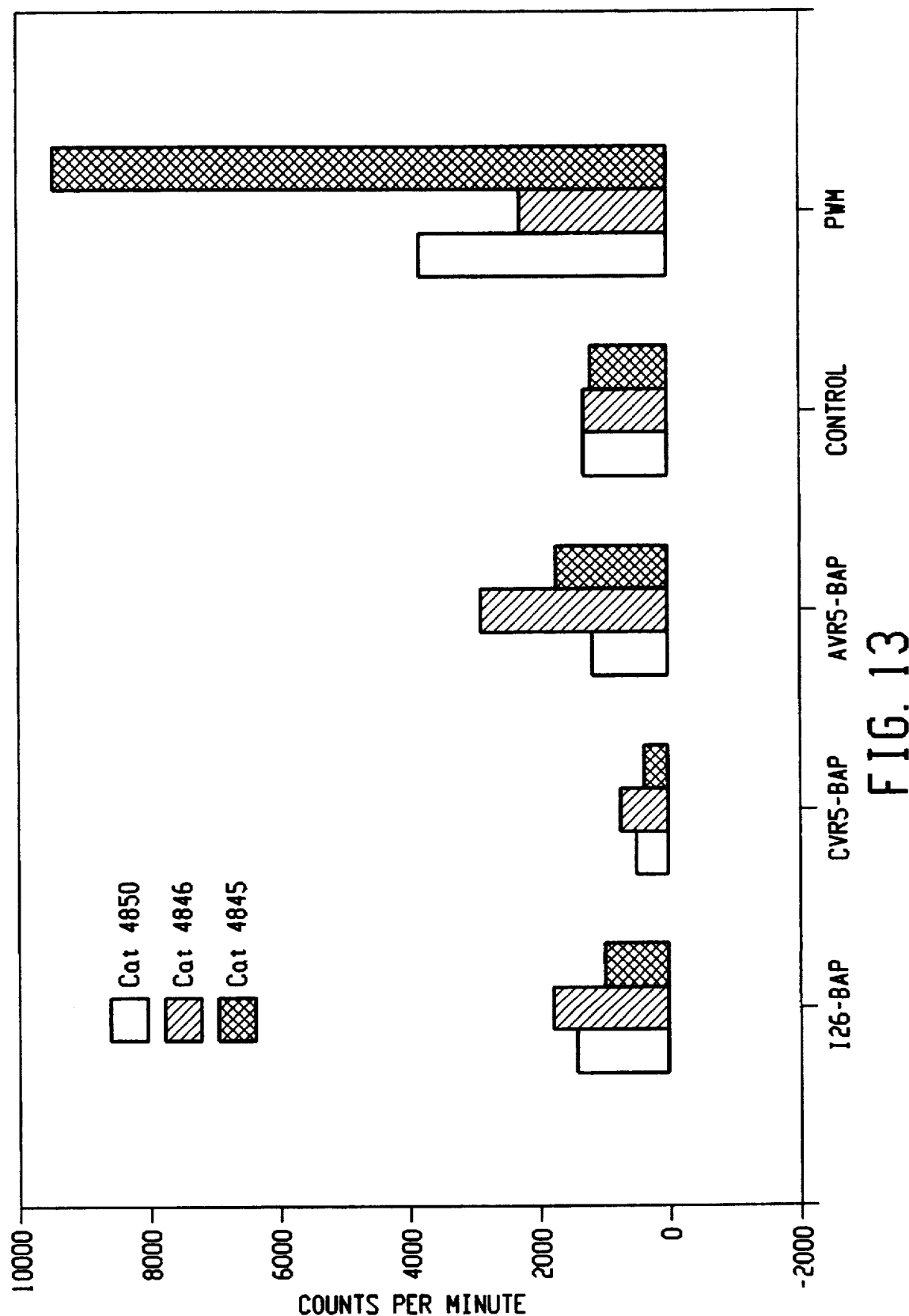
FIG. 13 is a graph showing the effect of $C_{Sarma}$VR5-BAP on stimulated feline peripheral blood lymphocytes; the plain rectangle represents Cat 4850; the one lined rectangle represents Cat 4846; and the two lined rectangle represents Cat 4845.

As shown in FIG. 12, neither $C_{Sarma}$VR5-BAP nor $A_{Glasgow1}$VR5-BNP significantly inhibited growth of the resting PBLs.

Stimulated PBLs Cultures

PBLs were isolated and seeded as described above. 5×10⁵M beta-mercaptoethanol, and sodium pyuvate were added to the culture media. $C_{Sarma}$VR5-BAP, I26-BAP or $A_{Glasgow1}$VR5-BNP at 6.0 μM concentration were added, cultured for five days and uptake of tritiated thymidine was used to measure cell proliferation rate. Pokeweed mitogen served as a positive control.

As shown in FIG. 13, $C_{Sarma}$VR5-BAP produced significantly lower uptake of tritiated thymidine, while $A_{Glasgow1}$VR5-BNP and I26-BNP did not alter uptake.

CEM Cultures

Human T4-Lymphoblastoid leukemia cells (CEM) were exposed to 0.001, 0.005, 0.025, 0.12, 0.6, 3.0, and 15.0 μM CVR5-BAP, $A_{Glasgow1}$VR5-BNP and I26-BAP and examined daily from 2 days post exposure to 6 days post exposure with the MTT assay.

The growth of the CEM cells was not significantly affected as compared to control cells by any of the branched apogenic peptides.

Feline Bone Marrow Cultures

Feline bone marrow cells were isolated after trochanteric bone marrow aspiration and phycol-hypaque density gradient centrifugation. Bone marrow cells were seeded at $1\times10^5$ cells per ml in 100 μl volumes in a 96 well plate. $C_{Sarma}$VR5-BAP or $A_{Glasgow1}$VR5-BNP at 6.0 μM concentration was added and samples were assayed by MTT at 0, 4, 18, and 21 hours post-exposure.

As shown in FIG. 14, neither $C_{Sarma}$VR5-BAP or $A_{Glasgow1}$VR5-BNP significantly inhibited growth of the cells.

Feline Thymocyte Cultures

Feline thymocytes were isolated from two cats at necropsy, suspended in media, and separated by phycol-hypaque density gradient centrifugation. Primary thymocytes were seeded at $1\times10^6$ cells per ml in 100 μl volumes in a 96 well plate. $C_{Sarma}$VR5-BAP or $A_{Glasgow1}$VR5-BNP at 6.0 μM concentration was added and samples were assayed by MTT at 0, 4, 18, and 21 hours post-exposure.

$C_{Sarma}$VR5-BAP significantly inhibited growth of the cells. In contrast, the $A_{Glasgow1}$VR5-BNP did not inhibit growth.

C1300H Cultures

A murine neuroblastoma cell line also designated "C1300H", was exposed to either 0.5, 1.0, 1.9, 3.8, 7.5, 15.0, and 30.0 μM CVR5-BAP, $A_{Glasgow1}$VR5-BNP or I26-BAP and examined on day 1 and day 4 post exposure with the MTT assay.

The C1300H cells were not significantly affected compared to control cells by any of the branched apogenic peptides.

TABLE I

SUMMARY OF $C_{SARMA}$VR5-BAP EFFECT ON VARIOUS CELL LINES

| Cell Line | Origin | Inhibitory Concentration | Exposure Time prior to Effect | Significance Level |
|---|---|---|---|---|
| 3201-Control | Feline T4-Lymphoma | 2.7 μM | 120 hours | $p < 0.05$ |
| 3201-FeLV-A | Feline T4-Lymphoma | 2.7 μM | 120 hours | $p < 0.05$ |
| 3201-FeLV-C | Feline T4-Lymphoma | 2.7 μM | 120 hours | $p < 0.05$ |
| HL60 | Human Promyelooyic Leukemia | 3.8 μM | <24 hours | $p < 0.01$ |
| H9 | Human T4-Lymphoblastoid Leukemia | 3.8 μM | <24 hours | $p < 0.01$ |
| K562 | Human Pluripotent Stem Cell Leukemia | 1.9 μM | <24 hours | $p < 0.05$ |
| F422 | Feline Lymphoma | 12 μM | <48 hours | $p < 0.05$ |
| MCC | Feline Large Granular Lymphocyte Lymphoma | 12 μM | <48 hours | $p < 0.05$ |
| Clone 81 | Feline Fibroblast | * | N.A. | N.S. |
| FEA-FeLV-A | Feline Fibroblast | * | N.A. | N.S. |
| HT1080 | Human Fibroblastoid | 6 μM | <48 hours | $p < 0.05$ |
| DH82 | Canine Histiocytic Lymphoma | ** | N.A. | N.S. |
| ERIC | Human T4-Lymphoblastoid Leukemia | ** | N.A. | N.S. |
| U937 | Human Histiocytic Lymphoma | 6 μM | <24 hours | $p < 0.05$ |
| CFU-E | Colony Forming Unit Erythroid Primary Feline Bone Marrow | 0.4 μM | N.A. | $p = 0.0053$ |
| BFU-E | Burst Forming unit Erythroid Primary Feline Bone Marrow | 0.04 μM | N.A. | $p = 0.06$ |
| CFU-GM | Colony Forming Unit-granulocyte Primary Feline Bone Marrow | ++ | N.A. | N.S. |
| EL-4 | Mouse Thymic Lymphoma cell line | <1.9 μM | <24 hours | |
| Keratinocytes | Primary human | <3.0 μM | <48 hours | |
| ciliary ganglia | primary cultures of chicken neurons | 12.0 μM | <24 hours | |
| FRTL5 | rat thyroid carcinoma cell line | 12.0 μM | <24 hours | |
| PBLs-Resting | primary feline peripheral blood lymphocytes-Resting | *** | N.A. | N.S. |
| PBLs-Stimulated | primary feline peripheral blood lymphocytes-Stimulated | 6.0 μM | 5 days | |
| CEM | Human T4-lymphoblastoid cell line | **** | N.A. | N.S. |
| Bone Marrow | Feline Primary Bone Marrow Culture | *** | N.A. | N.S. |

TABLE I-continued

SUMMARY OF C$_{SARMA}$VR5-BAP EFFECT ON VARIOUS CELL LINES

| Cell Line | Origin | Inhibitory Concentration | Exposure Time prior to Effect | Significance Level |
|---|---|---|---|---|
| Thymocytes | Feline Primary Thymocytes | 6.0 μM | <21 Hours | |
| C1300H | murine neuroblastoma cell line | + | N.A. | N.S. |

\*—No cytopathicity found; examined up to 100 μM concentration.
\*\*—No cytopathicity found; examined up to 2.7 μM concentration.
\*\*\*—No cytopathicity found; examined up to 6.0 μM concentration.
\*\*\*\*—No cytopathicity found; examined up to 15 μM concentration.
+—No cytopathicity found; examined up to 30 μM concentration.
++—No cytopathicity found; examined up to 4.0 μM concentration.

TABLE II

| Cell Line | Live (1 × 10$^5$ cells/ml) | Dead (1 × 10$^5$ cells/ml) | % Viable |
|---|---|---|---|
| Time = 4 hours | | | |
| HL-60 (Control) | 4.2 | 0 | 100 |
| HL-60 (AVR5-BAP) | 4.2 | 0 | 100 |
| HL-60 (C$_{Sarma}$VR5-BAP) | 5.0 | 0.6 | 90 |
| H-9 (Control) | 5.6 | 0.2 | 97 |
| H-9 (AVR5-BAP) | 4.8 | 0.2 | 97 |
| H-9 (C$_{Sarma}$VR5-BAP) | 4.4 | 0.4 | 92 |
| Time = 24 hours | | | |
| HL-60 (Control) | 7.6 | 0 | 100 |
| HL-60 (AVR5-BAP) | 9.0 | 0 | 100 |
| HL-60 (C$_{Sarma}$VR5-BAP) | 4.4 | 1.0 | 81 |
| H-9 (Control) | 9.8 | 0.9 | 92 |
| H-9 (AVR5-BAP) | 7.6 | 0.6 | 93 |
| H-9 (C$_{Sarma}$VR5-BAP) | 7.8 | 0.8 | 90 |
| Time = 48 hours | | | |
| HL-60 (Control) | 10.4 | 0.6 | 95 |
| HL-60 (AVR5-BAP) | 10.2 | 0 | 100 |
| HL-60 (C$_{Sarma}$VR5-BAP) | 5.6 | 3.4 | 62 |
| H-9 (Control) | 15.6 | 0.6 | 95 |
| H-9 (AVR5-BAP) | 17.0 | 0.4 | 98 |
| H-9 (C$_{Sarma}$VR5-BAP) | 13.0 | 1.8 | 88 |
| Time = 72 hours | | | |
| HL-60 (Control) | 16.4 | 0.2 | 99 |
| HL-60 (AVR5-BAP) | 14.0 | 0.2 | 99 |
| HL-60 (C$_{Sarma}$VR5-BAP) | 9.2 | 2.0 | 82 |
| H-9 (Control) | 19.8 | 0.1 | 93 |
| H-9 (AVR5-BAP) | 11.8 | 0.8 | 92 |
| H-9 (C$_{Sarma}$VR5-BAP) | 14.2 | 2.2 | 86 |

Biochemical Analysis of C$_{Sarma}$VR5-BAP Treated Cells-Cytokine Release

Cell cultures of HL60 cells, K562 cells and H9 cells were treated with 3 μM C$_{Sarma}$VR5-BAP. At 24 hours after treatment, the cell cultures were centrifuged and the supernatant was collected. The supernatant was analyzed for Interleukin -1, Interleukin -6 and tumor necrosis factor-α (hereinafter also referred to as "TNFα"). IL-1, IL-6, and TNFα were assayed by enzyme linked immunosorbent assay with commercially available kits such as Factor-Test HTNFα, from Genzyme, Cambridge, Mass.

The HL60, K562, and H9 cells released IL-6 but not IL-1 or TNFα into the culture supernatant after 24 hours exposure to C$_{Sarma}$VR5-BAP. The HL60 cell culture supernatant had 6.62±6.18/ml IL-6 before treatment and 85.2±28.2/ml IL-6 after treatment with C$_{Sarma}$VR5-BAP. H9 cell culture supernatants had undetectable levels of IL-6 prior to treatment and 80.4±28.0/ml IL-6 after treatment. K562 cell cultures had undetectable levels of IL-6 prior to treatment and 80.4±17.9/ml IL-6 after treatment with C$_{Sarma}$VR5-BAP. In a separate experiment, U937 cells released TNFα into the cell culture supernatant after 24 hours of exposure to 2.7 μM C$_{Sarma}$VR5-BAP. U937 cell cultures had 0.0±0.0/ml TNFα prior to exposure and 92+9.9/ml TNFα after exposure to C$_{Sarma}$VR5-BAP. U937 cell cultures has undetectable levels of TNFα both before and after exposure to A$_{Glasgow1}$VR5-BAP.

Augmentation of differentiation by 1,25-dihydroxycholecalciferol 1,25-dihydroxycholecalciferol, also referred to as 1,25-dihydroxy vitamin D$_3$, is the active metabolite of vitamin D$_3$ and controls calcium transport and gene expression in many cells. At 1 μM, 1,25-dihydroxy vitamin D$_3$ will drive differentiation of HL60 cells into monocytes; overt differentiation requires 72–96 hours. Accordingly, HL60 cell cultures were simultaneously exposed to a subapoptotic dose of 1 μM C$_{Sarma}$ VR5-BAP and 0.5 or 1.0 μM 1, 25-dihydroxy vitamin D$_3$. The cultures were then evaluated by inverted phase microscopy of tissue culture plates and by light microscopic examination of Wright-Giemsa stained cytocentrifuge preparations.

In cell cultures treated with 1.0 μM 1,25-dihydroxy vitamin D$_3$ and 1 μM C$_{Sarma}$VR5-BAP, more than 50% of HL60 cells were apoptotic by 48 hours. Such cells had widespread nuclear condensation and fragmentation, cytoplasmic condensation, and surface blebbing and fragmentation. In cultures treated with 0.5 μM, 1,25-dihydroxy vitamin D$_3$ and 1 μM C$_{Sarma}$VR5-BAP, changes were similar but slower to progress; nuclear condensation was demonstrable by 48–72 hours, but frank apoptosis and differentiation were not seen until after 96 hours of treatment. Thus, simultaneous exposure to 1,25-dihydroxy vitamin D$_3$ increases the sensitivity of HL60 cells to C$_{Sarma}$VR5-BAP six-fold. These data suggest C$_{Sarma}$VR5-BAP modulates intracellular calcium levels.

Neither sodium butyrate nor retinoic acid induce apoptisis with sub-apoptotic doses of C$_{Sarma}$VR5-BAP At 1 μM sodium butyrate and retinoic acid induce monocytic and granulocytic differentiation in HL60 cells, respectively. Neither the sodium butyrate nor retinoic acid is specifically associated with calcium transport. HL60 cells were simultaneously exposed to such apoptotic dose (1 μM) of $C_{Sarma}$VR5-BAP and to either 1 μM sodium butyrate or 1 μM retinoic acid. Cells were cultured for 5 days and evaluated by inverted phase contrast microscopy and light microscopic examination of Wright-Giemsa-Stained cytrocentrifuge preparation. Samples were taken at 2, 3 and 5 days.

The results showed the simultaneous treatment of HL60 cells with 1 μM $C_{Sarma}$VR5-BAP and either 1 μM sodium butyrate or 1 μM retinoic acid did not cause apoptosis. No differences were seen between treated cultures and control cultures.

A commonly used anti-apogenic compound is zinc. HL60, K562, 3201 and H9 cells were exposed to 1, 2, 4, 7.9, 15.7, 31.3, 62.5, 125, 250, 500, and 1000 µM zinc sulfate and 6 µM $C_{Sarma}$VR5-BAP. The cells were cultured for 24 and 8 hours.

Zinc sulfate failed to reverse $C_{Sarma}$VR5-BAP induced apoptosis in the cells. Direct toxicity of zinc sulfate was noted at concentrations greater than 31.3 µM.

The failure $C_{Sarma}$VR5-BAP effect to be reversed by interleukin-1 distinguishes $C_{Sarma}$ VR5-BAP from other calcium-modulating apogens such as A23187. As zinc prohibits the effect of many apogens, it may be that $C_{Sarma}$-VR5-BAP triggers apoptosis by a calcium dependant but otherwise unique mechanism.

Heparin Reversed $C_{Sarma}$VR5-BAP Induced Apoptosis.

HL60 cell cultures were treated with 6 µM $C_{Sarma}$VR5-BAP and 0.3 U/ml, or 3.0 U/ml heparin. Control cell cultures received either no polypeptide or 0.3 U/ml or 3.0 U/ml heparin. Cell growth was determined at 1 and 2 days as assessed by MTT cell proliferation/viability assay. The mobilization of intracellular calcium was assessed by INDO-1 staining and anchored cell fluorescent microscopy.

Heparin inhibited the growth suppression of 6 µM $C_{Sarma}$VR5-BAP on the cell cultures at concentrations greater than or equal to 0.3 U/ml. Thus the only known inhibitor of apoptosis induced by $C_{Sarma}$ VR5-BAP is heparin. Heparin also prevents mobilization of intracellular calcium.

Effect of $C_{Sarma}$VR5-BAP on Isolated DNA or Nuclei

To demonstrate the interaction between DNA and $C_{Sarma}$VR5-BAP, a reaction mixture containing 5 µM $MgCl_2$ or 5 µM $CaCl_2$ in 10 µM, Tris pH 7.7, was prepared. The DNA was either isolated K562 typing grade DNA #4410SA, available from GIBCO, or λ DNA BRL, catalog #5250SA from Gibco, or HL60 genomic DNA isolated by conventional phenol chloroform/enzymatic procedures. $C_{Sarma}$VR5-BAP or $A_{Glasgow1}$VR5-BAP was added at final concentrations of 6, 60, or 600 µM. 1 µM of DNA was added and the final reaction mixture volume was 25 µl. The DNA was then electrophoresed on 2% agarose gels for 120 minutes and viewed under UV light transillumination.

$C_{Sarma}$VR5-BAP intercalates with DNA. The interaction of $C_{Sarma}$VR5-BAP with DNA prevents standard ethidium bromide staining of DNA in agarose gels viewed by ultraviolet light transillumination. This is not due to a direct nuclease or DNA degradative effect; the DNA remains undegraded despite protracted incubation 4 to 6 hours, with the $C_{Sarma}$VR5-BAP or $A_{Glasgow1}$VR5-BAP. The interaction between the DNA and the $C_{Sarma}$VR5-BAP is probably due to protruding basically charged amino acid residues on the $C_{Sarma}$VR5-BAP. The lack of direct nuclease activity of $C_{Sarma}$ VR5-BAP distinguishes it from certain other apoptosis-inducing agents like diphtheria toxin.

To determine whether $C_{Sarma}$VR5-BAPa induces or activates an endogenous, that is a host cellular, nuclease, K562 and HL60 nuclei were isolated by hypotonic lysis in 1.5 mM $MgCl_2$ and incubated with either 6, 60, or 600 µM $C_{Sarma}$VR5-BAP. For comparison, other cell cultures were treated with facilitators like adenosine triphosphate, glycerol, or heat shock protein. The DNA was subsequently extracted from the nuclei and electrophoresed in 2% agarose gels.

No DNA degradation was evident and no differences were seen between DNA extracted from $C_{Sarma}$VR5-BAP treated nuclei and control isolated nuclei.

Calmodulin Binding Data

The binding of the branched apogenic peptide to calmodulin was evaluated in a non-denaturing polyacrylamide gel electrophoresis procedure. 10 µl of calmodulin solution from Calbiochem, which contains about 0.5 mg in 20 mM tris, at pH 7.2, was incubated for 60 minutes at room temperature with 15 µl binding buffer and 5 µl of a 1 mM peptide solution. Calcium was added to the cultures at 0.2 mMol. Bromophenol blue was added as a tracking dye, the sample was loaded and electrophoresed on a 12.5% acrylamide gel at 18 mAmps for 20 hours. The branched apogenic peptide binding of calmodulin was measured as a shift in migration rate as compared to calmodulin alone.

$C_{Sarma}$VR5-BAP bound to calmodulin in both the presence and absence of calcium. In contrast, neither the $A_{Glasgow1}$VR5-BNP or $C_{Sarma}$VR5 chain bound to calmodulin.

Intracellular Messengers

To identify the intracellular messengers that result in apoptosis after stimulation by $C_{Sarma}$VR5-BAP, the intracellular free calcium was measured in HL60 cells, H9 cells, and K562 cells by real time confocal microscopy using an ACAS 570, from Meridian Instrument, Meridian Miss. Four µL of a 1 mg/ml solution of the fluorescent calcium probe INDO-1-AM from Molecular Probes, Eugene, Oreg., was added to $1\times10^6$ cells after washing in INDO-1 buffer, that is Gibco BRL buffer, and incubated at 37° C. for 30 minutes. The cells were washed, and adhered to coverslip chambers using cell-tak in a 0.1M sodium bicarbonate buffer for 30 minutes. The cleavage of the acetylmethyl group from INDO-1 causes retention of the fluorescent probe in the cytoplasm and allows measurement of the emission of the unbound dye to the calcium bound dye. The excitation wavelength for INDO-1 is 350 nm which fluoresces at 40 nm when calcium is bound while the unbound emission is 480 nm. The results are presented as an emission ratio, with values greater than 1.0 representing significant elevation in the intracellular calcium.

The addition of 6.0 µM $C_{Sarma}$VR5-BAP in HL60 cells caused a significant increase in the intracellular calcium in 30 to 90 seconds. In contrast, in H9 and K562 cells, the elevation in intracellular calcium occurred after 8 to 10 minutes. Cells without peptide added or cells with 6.0 µM $A_{Glasgow1}$VR5-BNP did not exhibit any change in the intracellular calcium levels. The free peptides $C_{Sarma}$VR5 and $A_{Glasgow1}$VR5 at 48 µM levels also did not cause any changes in intracellular calcium.

In a second experiment, H9 cells were incubated with the ratioactive calcium isotope $Ca^{45}$ and exposed to 10 µM CVR-BAP or 10 µM $A_{Glasgow1}$VR5-BNP.

Significant elevations in the amount of $Ca^{45}$ trapped inside the cell after centrifugation through mineral oil at 60 to 90 seconds post exposure to $C_{Sarma}$VR5-BAP but not $A_{Glasgow1}$VR5-BNP. This experiment demonstrated significant entry of extracellular calcium after exposure to $C_{Sarma}$VR5-BAP. Evaluation of ENCFE6VR5K3-BAP on Cell Growth HL60, H9, 3201, and U937 cells cultures were exposed to 0, 3.0, 6.0, an 12.0 µM ENCFE6VR5K3-BAP. Cell growth was determined by MTT assay at 24 hours.

By 24 hours after exposure to ENCFE6VR5K3-BAP, all four cell lines cultures were at or below 52% of control growth levels.

Evaluation of ENCFE6VR5-BAP on Cell Growth

HL60, H9, 3201, and U937 cells cultures were exposed to 0, 3.0, 6.0, an 12.0 µM ENCFE6VR5N3-BAP. Cell growth was determined by MTT assay at 24 hours.

By 24 hours after exposure to ENCFE6VR5N3-BAP, all four cell lines were at or below 54% of control growth values except for 3201 cells at 6 µM concentration. The 3201 cell required 12 μM concentrations for the MTT value to fall to 27% of controls.

Evaluation of CVR5N3-BAP on Cell Growth

HL60 cell cultures were exposed to 6.0 μM $C_{Sarma}$VR5-BAP or CVR5N3-BAP for 24 hours and examined by the MTT assay. Control cultures received no branched apogenic peptide.

The growth of the HL60 cells was inhibited by both $C_{Sarma}$VR5-BAP and CVR5N3-BAP as compared to controls.

What is claimed is:

1. A branched apogenic peptide comprising:
   a. a core having at least 3 amino acids;
   b. at least four peptide chains, connected to said core, each peptide chain having from 7 to 25 amino acids comprising the following amino acid sequence:

ZXXZXXZ, SEQ.ID.NO.6, wherein: Z is arginine, lysine or any positively charged synthetic amino acid; and X is any amino acid; and
wherein the branched peptide induces apoptosis.

2. The invention of claim 1, wherein the core has at least seven amino acids and there are at least eight peptide chains attached to the core.

3. The invention of claim 1, wherein each X is selected from the group consisting of threonine, glutamine, glycine and histidine.

4. The invention of claim 2, wherein the peptide chain comprises the following amino acid sequence:

LCKKTQKGHKGTHYL, SEQ.ID.NO.3, wherein: K is lysine; T is threonine; L is leucine; C is cysteine; Q is glutamine; G is glycine; H is histidine; and Y is tyrosine.

5. The invention of claim 2, wherein the peptide chain comprises the following amino acid sequence:

LCNKTQKGHKGTHYL, SEQ.ID.NO.1, wherein: K is lysine; T is threonine; L is leucine; C is cysteine; Q is glutamine; G is glycine; H is histidine; Y is tyrosine; and N is asparagine.

6. The invention of claim 2, wherein the peptide chain comprises the following amino acid sequence:

LCNKTQKGHRGTHYL, SEQ.ID.NO.4, wherein: K is lysine; T is threonine; L is leucine; C is cysteine; Q is glutamine; G is glycine; H is histidine; Y is tyrosine; N is asparagine; and R is arginine.

7. The invention of claim 2, wherein the peptide chain comprises the following amino acid sequence:

LCKKTQKGHRGTHYL, SEQ.ID.NO.5, wherein: K is lysine; T is threonine; L is leucine; C is cysteine; Q is glutamine; G is glycine; H is histidine; Y is tyrosine; and R is arginine; and the core amino acids are lysines.

8. A method for inducing apoptosis in vitro in cells and in vivo in erythrocyte progenitor cells and lymphocyte progenitor cells comprising the following steps:
   a. providing a branched apogenic peptide comprising:
      a. a core having at least 3 amino acids;
      b. at least four peptide chains, connected to said core, each peptide chain having from 7 to 25 amino acids and comprising the following amino acid sequence:

Z X X Z, SEQ.ID. NO.2, wherein: Z is arginine or lysine or any positively charged amino acid; and X is any amino acid, and b. administering the branched apogenic peptide to the cells, wherein the cells undergo apoptosis or reduced proliferation.

9. The invention of claim 8, wherein the core has at least 7 amino acids and there are at least eight peptide chains attached to the core.

10. The invention of claim 9, wherein the peptide chain comprises the following amino acid sequence:

LCKKTQKGHKGTHYL, SEQ.ID.NO.3, wherein: K is lysine; T is threonine; L is leucine; C is cysteine; Q is glutamine; G is glycine; H is histidine; and Y is tyrosine; and the core amino acids are lysines.

11. The invention of claim 9, wherein the peptide chain comprises the following amino acid sequence:

LCNKTQKGHKGTHYL, SEQ.ID.NO.1, wherein: K is lysine; T is threonine; L is leucine; C is cysteine; Q is glutamine; G is glycine; H is histidine; Y is tyrosine; and N is asparagine; and the cone amino acids are lysines.

12. The invention of claim 9, wherein the peptide chain comprises the following amino acid sequence:

LCNKTQKGHRGTHYL, SEQ.ID.NO.4, wherein: K is lysine; T is threonine; L is leucine; C is cysteine; Q is glutamine; G is glycine; H is histidine; Y is tyrosine; N is asparagine; and R is arginine; and the cone amino acids are lysines.

13. The invention of claim 9, wherein the peptide chain comprises the following amino acid sequence:

LCKKTQKGHRGTHYL, SEQ.ID.NO.5, wherein: K is lysine; T is threonine; L is leucine; C is cysteine; Q is glutamine; G is glycine; H is histidine; Y is tyrosine; and R is arginine.

14. A pure peptide having a sequence selected from the group consisting of: LCKKTQKGHKGTHYL, SEQ.ID.NO.3; LCNKTQKGHKGTHYL, SEQ.ID.NO.1; LCNKTQKGHRGTHYL, SEQ.ID.NO.4; and LCKKTQKGHRGTHYL, SEQ.ID.NO.5.

15. The peptide of claim 14 wherein the peptide has the following amino acid sequence:

LCKKTQKGHKGTHYL, SEQ.ID.NO.3, wherein: K is lysine; T is threonine; L is leucine; C is cysteine; Q is glutamine; G is glycine; H is histidine; and Y is tyrosine.

16. The invention of claim 14, wherein the peptide has the following amino acid sequence:

LCNKTQKGHKGTHYL, SEQ.ID.NO.1, wherein: K is lysine; T is threonine; L is leucine; C is cysteine; Q is glutamine; G is glycine; H is histidine; Y is tyrosine; and N is asparagine.

17. The invention of claim 14, wherein the peptide has the following amino acid sequence:

LCNKTQKGHRGTHYL, SEQ.ID.NO.4, wherein: K is lysine; T is threonine; L is leucine; C is cysteine; Q is glutamine; G is glycine; H is histidine; Y is tyrosine; N is asparagine; and R is arginine.

18. The invention of claim 14, wherein the peptide has the following amino acid sequence:

LCKKTQKGHRGTHYL, SEQ.ID.NO.5, wherein: K is lysine; T is threonine; L is leucine; C is cysteine; Q is glutamine; G is glycine; H is histidine; Y is tyrosine; and R is arginine.

* * * * *

UNITED STATES PATENT AND TRADEMARK OFFICE
CERTIFICATE OF CORRECTION

PATENT NO. : 5,591,717
DATED : January 7, 1997
INVENTOR(S) : Rojko, et al.

It is certified that error appears in the above-indentified patent and that said Letters Patent is hereby corrected as shown below:

On the Title page, item [73]:

Assignee: The Ohio State Research Foundation, Columbus, Ohio
Attorney, Agent or Firm should read --
           Calfee, Halter & Griswold --.

Signed and Sealed this

Second Day of September, 1997

Attest:

Attesting Officer

BRUCE LEHMAN

Commissioner of Patents and Trademarks